(12) United States Patent
Malkin et al.

(10) Patent No.: US 6,391,259 B1
(45) Date of Patent: May 21, 2002

(54) OZONE APPLICATIONS FOR DISINFECTION, PURIFICATION AND DEODORIZATION

(75) Inventors: Boris Malkin; Gena Perlov; Shmuel Yannai, all of Haifa (IL)

(73) Assignee: Ozontech Ltd., Nesher (IL)

( * ) Notice: Subject to any disclaimer, the term of this patent is extended or adjusted under 35 U.S.C. 154(b) by 0 days.

(21) Appl. No.: 09/202,585

(22) PCT Filed: Jun. 26, 1997

(86) PCT No.: PCT/IL97/00214

§ 371 Date: Dec. 17, 1998

§ 102(e) Date: Dec. 17, 1998

(87) PCT Pub. No.: WO98/01386

PCT Pub. Date: Jan. 15, 1998

(30) Foreign Application Priority Data

Jun. 26, 1996 (IL) .................................................. 118741

(51) Int. Cl.$^7$ .......................... A01N 2/00; B01D 15/00; B03C 3/00; C01B 13/10
(52) U.S. Cl. ..................... 422/28; 422/128; 422/186.11; 422/186.14; 422/186.25; 210/198.1; 210/748; 210/760; 96/69; 95/59; 204/176
(58) Field of Search ................................ 422/1, 28, 29, 422/31, 32, 33, 907, 186.07, 20, 186.11, 128, 186.14, 127, 186.25, 906; 210/760, 748, 198.1; 96/69; 95/59; 204/176

(56) References Cited

U.S. PATENT DOCUMENTS

| | | | |
|---|---|---|---|
| 1,044,700 A | * 11/1912 | Small et al. | |
| 1,166,588 A | 1/1916 | Hoffman | 426/307 |
| 1,215,254 A | 2/1917 | Darden | 426/312 |
| 1,575,348 A | 3/1926 | Luscher | 426/320 |
| 2,379,677 A | 7/1945 | Borsakovsky | 99/153 |
| 2,901,356 A | 8/1959 | Gallotti | 99/155 |
| 3,341,335 A | 9/1967 | Eolkin et al. | 99/150 |
| 3,622,492 A | * 11/1971 | Kinney | 204/322 |
| 3,897,210 A | 7/1975 | Gruber et al. | 21/58 |
| 4,076,617 A | * 2/1978 | Bybel et al. | 210/19 |
| 4,226,179 A | 10/1980 | Sheldon, III et al. | 99/475 |
| 4,402,813 A | * 9/1983 | Kircher et al. | 204/279 |
| 4,519,357 A | 5/1985 | McAllister | 123/539 |
| 4,549,477 A | 10/1985 | McCabe, Jr. | 99/477 |
| 4,614,573 A | 9/1986 | Masuda | 204/176 |
| 4,789,801 A | 12/1988 | Lee | 310/308 |
| 4,863,701 A | * 9/1989 | McMurray | 422/186.08 |
| 4,898,679 A | 2/1990 | Siegel et al. | 210/752 |
| 4,933,411 A | 6/1990 | Gifford | 426/399 |
| 4,954,321 A | * 9/1990 | Jensen | 422/186.19 |
| 5,011,699 A | 4/1991 | Mitsuda et al. | 426/320 |
| 5,053,140 A | 10/1991 | Hurst | 210/704 |
| 5,102,629 A | * 4/1992 | Hayashi et al. | 422/186.18 |
| 5,212,140 A | * 5/1993 | Yoshimoto et al. | 502/300 |
| 5,227,184 A | 7/1993 | Hurst | 426/312 |
| 5,236,672 A | * 8/1993 | Nunez et al. | 422/186.04 |
| 5,352,467 A | 10/1994 | Mitchell et al. | 426/316 |
| 5,431,939 A | 7/1995 | Cox et al. | 426/300 |

(List continued on next page.)

Primary Examiner—Robert J. Warden, Sr.
Assistant Examiner—Monzer R. Chorbaji
(74) Attorney, Agent, or Firm—Mark M. Friedman

(57) ABSTRACT

A frame-type ozone generator (242) has a plurality of elongated electrodes (201, 202) deployed in substantially parallel, spaced relation to each other so as to form a substantially flat electrode array, and a flow generator (241) for generating a flow of oxygen containing gas through the electrode array in a direction substantially perpendicular to the electrode array. Each of the electrodes is formed from an electrically conductive core (211) covered with polyvinyl-difluoride (212). Preferably, each electrode array is arranged within a frame (206) of a given area. Also disclosed are an apparatus for treating a product with ozone-containing gas in which pressure-waves are used to enhance effectiveness of the ozone treatment, and a two-chamber batch method for implementing treatment of a product with possibly harmful gases such as ozone.

26 Claims, 42 Drawing Sheets

U.S. PATENT DOCUMENTS

| | | | |
|---|---|---|---|
| 5,447,640 A | | 9/1995 | Omi et al. .................. 210/748 |
| 5,466,425 A | * | 11/1995 | Adams .................... 422/186.3 |
| 5,529,760 A | * | 6/1996 | Burris ................... 422/186.07 |
| 5,545,380 A | * | 8/1996 | Gray .................... 422/186.07 |
| 5,597,599 A | | 1/1997 | Smith et al. ................ 426/316 |
| 5,609,736 A | * | 3/1997 | Yamamoto .................. 204/164 |
| 5,630,915 A | * | 5/1997 | Greene et al. ............. 204/164 |
| 5,683,576 A | * | 11/1997 | Olsen ........................ 210/138 |

* cited by examiner

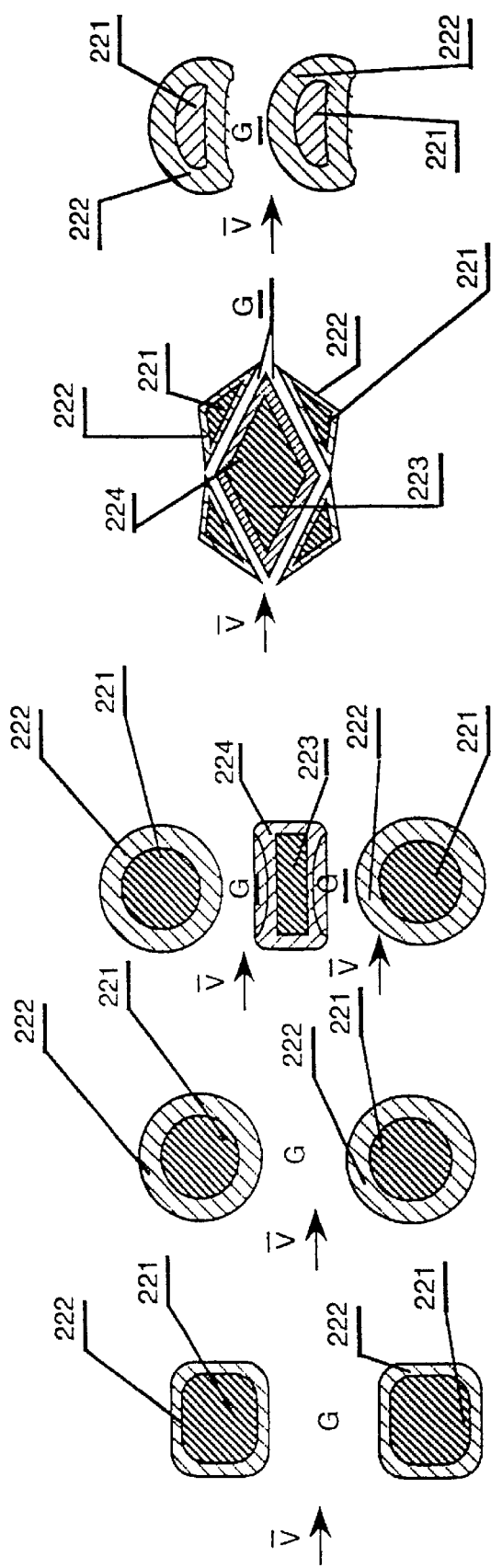

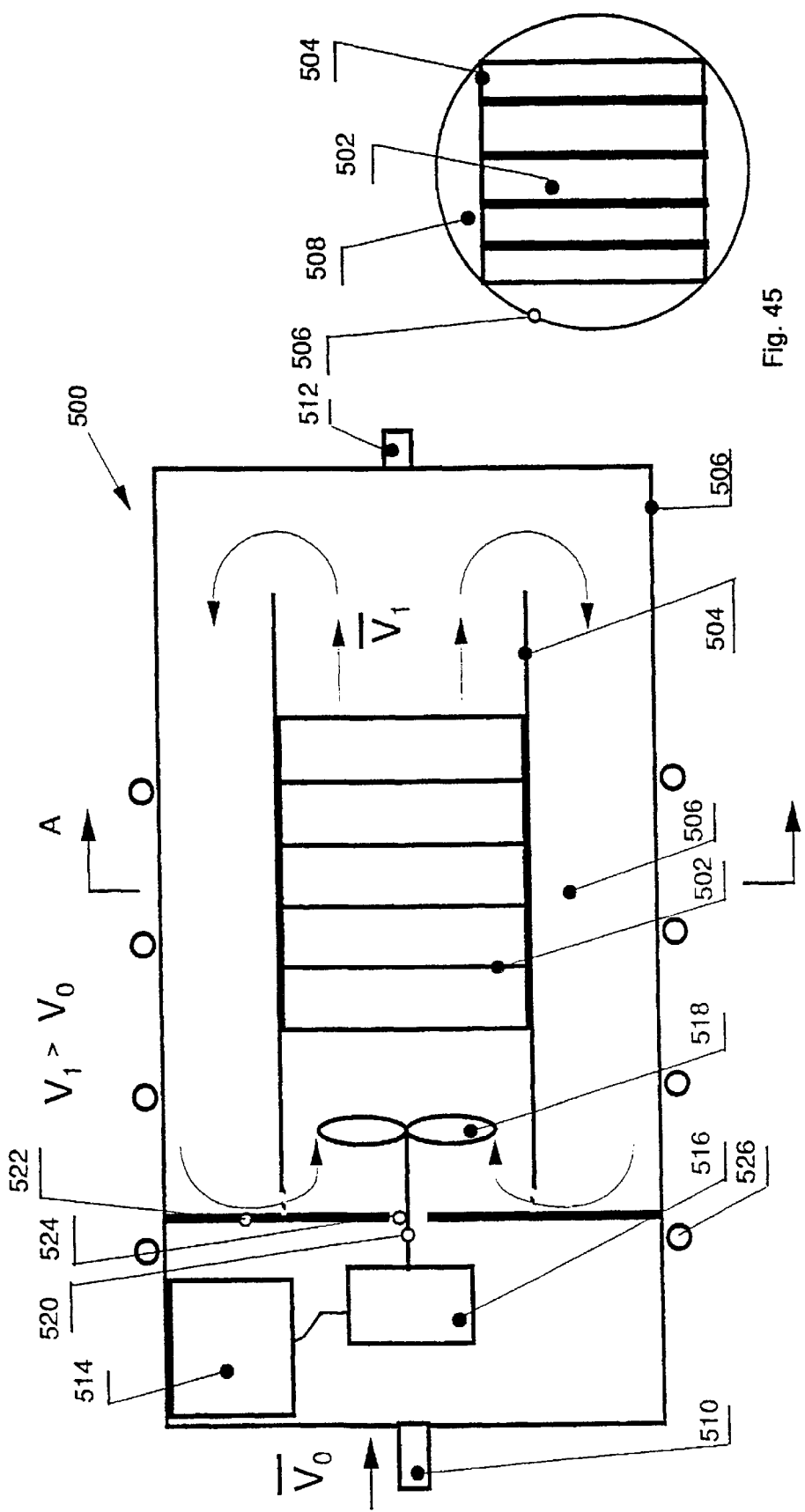

OZONE APPLICATIONS FOR DISINFECTION, PURIFICATION AND DEODORIZATION

FIELD AND BACKGROUND OF THE INVENTION

The present invention relates to a system for disinfection, purification and deodorization, using a gaseous phase containing ozone. More particularly, the invention relates to said system, wherein the above operations are carried out on the surface of the respective objects to be treated.

The disinfection treatment with ozone of solid objects, such as fresh agricultural produce, drugs and medical and industrial equipment, is well known, being carried out in a gaseous form or in an aqueous solution. Among the main disadvantages of this treatment for agricultural produce the following can be mentioned:

(a) Possible damage to certain kinds of agricultural produce due to interaction with the surface of the treated material and, (b) Diffusion of ozone into the treated tissue. in case of non-agricultural solid objects, such as: drugs as well as food products, the following can be mentioned:

(c) There are parts on the objects to be treated where there are stagnant regions, i.e. no free flowing gas, so that the ozone penetration is inefficient.

Among the disadvantages of treatment in a liquid phase, the following can be mentioned:

(a) It is impractical to wet the products to be treated and then to dry them again.

(b) There are products, the surface of which may be affected after their immersion in a liquid, the surface area may be affected. Thus, the cuticle coating the egg shell may dissolve in an aqueous solution and as a result the treated egg may lose a large amount of water during subsequent storage.

(c) Metallic parts may undergo corrosion after the treatment in a liquid phase.

(d) Fruits and vegetables possessing a plume may lose it and as a result, become less attractive.

The importance of the above problem, is evidenced by the relatively large number of patents and papers dealing therewith. Thus, according to Chemical Abstract Vol.123: 8355. an apparatus is disclosed for sterilization of food by its immersion in water, where a stream of ozone and air is bubbled continuously into the water.

According to the recent U.S. Pat. No. 5,403,602, the process utilizes an aqueous solution containing 3% to 12% ozone. The released ozone reacts with the food constituents, being controlled by the introduction of an enzyme catalyst. This sterilization process is claimed to be most useful for aseptic packaging of fresh food.

According to Chemical Abstract Vol.119:15419, an apparatus is described for sterilizing fluids, consisting of an ozone chamber in which ozone is generated and then dispersed throughout the ozone-air mixture by a diffuser. The fluid and ozone are thoroughly mixed in a chamber and radiates the fluid to be treated. As claimed this apparatus is useful for food processing, farming and water or air purification plants.

According to Chemical Abstract Vol.116:261655, odorous air or water in refrigerating cases used for displaying fish and other foods, is deodorized by injecting ozone in a system comprising means for gaseous or liquefied ozone in a pressure vessel connected to the refrigeration cases. It is stipulated, that bacterial growth and malodor formation inside the refrigeration cases can be significantly lowered.

According to Chemical Abstract Vol.116:234256, a method and apparatus are described for sterilizing vegetables and fish using an aqueous ozone solution at a pH in the range of 3.5–4.5. This pH range is maintained by addition of an organic acid, such as acetic acid, the ozone solution controlling the microorganisms growth.

The above brief review clearly illustrates the existence of the problem and need for disinfection, purification and deodorization of fresh agricultural produce, drugs, and medical and industrial equipment using ozone.

It is an object of the present invention to provide a system for disinfection, purification and deodorization of the objects kept in a treatment space, using ozone. It is another object of the present invention to provide a system for disinfection, purification and deodorization of said objects, which overcome the existing drawbacks of the known systems.

SUMMARY OF THE INVENTION

A first aspect of the present invention relates to a system for disinfection, purification and deodorization of the surface of objects kept in a treatment space. by a forced stream of gaseous ozone mixed homogeneously with a carrier gas, flowing on the said surface, said flow being assisted by acoustic waves.

According to a preferred embodiment, the acoustic waves are produced through an acoustic transducer.

Thus, according to the teachings of the present invention there is provided, a frame-type ozone generator comprising: (a) a plurality of elongated electrodes deployed in substantially parallel, spaced relation to each other so as to form a substantially flat electrode array; and (b) a flow generator for generating a flow of oxygen containing gas through the electrode array in a direction substantially perpendicular to the electrode array, wherein each of the electrodes is formed from an electrically conductive core covered with polyvinyldifluoride.

According to a further feature of the present invention, the electrode array is arranged within a frame of a given area, the frame being configured for assembly with other similar frames to form an extended ozone generator of area greater than the given area.

According to a further feature of the present invention, the frame is substantially rectangular having first and second sides substantially perpendicular to the electrodes, the first and second sides being formed with complementary interlocking forms such that the first side could be engaged with a juxtaposed second side of a similar frame to form an extended ozone generator unit.

According to a further feature of the present invention, the first side includes a first common electrical connection to a first set of the electrodes, the complementary interlocking forms being configured such that the first common electrical connection would make electrical contact with another common electrical connection of a similar frame juxtaposed so as to interlock with the frame.

According to a further feature of the present invention, the frame has first and second ends substantially parallel to the electrodes, the first and second ends being formed with complementary interlocking shapes such that the first end could be engaged with a juxtaposed second end of a similar frame to form an extended ozone generator unit.

According to a further feature of the present invention, the first end includes a first common electrical connection to a first set of the electrodes, the complementary interlocking shapes being configured such that the first common electrical connection would make electrical contact with a common electrical connection of a similar frame juxtaposed so as to interlock with the frame.

According to a further feature of the present invention, the frame and the electrode array are integrally formed from molded polyvinyl-difluoride with electrically conductive implants.

There is also provided according to the teachings of the present invention. an apparatus for treating a product with ozone-containing gas, the apparatus comprising: (a) a container for containing the product; (b) an ozone generator for supplying ozone-containing gas to the interior of the container; and (c) a pressure-wave generator for generating pressure waves within the container so as to enhance effectiveness of the ozone treatment.

According to a further feature of the present invention, there is also provided a flow generating system for generating circulation of the ozone-containing gas.

According to a further feature of the present invention, there is also provided a flow generating system configured so as to generate a flow of the ozone-containing gas which alternates between a first direction and a second direction opposite to the first direction.

According to a further feature of the present invention, there is also provided a flow generating system configured so as to generate simultaneous flows of the ozone-containing gas in more than one direction towards the product.

According to a further feature of the present invention, there is also provided a cooling system for cooling at least a surface layer of the product prior to treatment sufficiently to cause condensation of ozone-containing water vapor on the surface layer.

According to a further feature of the present invention there is also provided a cooling system for cooling at least a surface layer of the product prior to treatment sufficiently to cause freezing of ozone-containing water vapor on the surface layer.

According to a further feature of the present invention, the product is water. the apparatus also including a water management system for generating a moving film of water within the container.

According to a further feature of the present invention, the product is water, the apparatus also including: (a) a spray generator for producing a spray of water moving in a first direction within the container; and (b) a flow generating system for generating a flow of the ozone-containing gas in a direction substantially opposite to the first direction.

According to a further feature of the present invention, there is also provided a catalytic filter associated with the container for removing ozone from the ozone-containing gas prior to opening of the container.

There is also provided according to the teachings of the present invention, a method for batch treatment of a product with a potentially harmful gas, the method comprising: (a) providing first and second treatment chambers; (b) treating a first batch of the product with a quantity of the gas within the first treatment chamber; (c) positioning a second batch of the product within the second treatment chamber; and (d) transferring from the first treatment chamber to the second treatment chamber at least part of the quantity of the gas.

According to a further feature of the present invention, the potentially harmful gas is an ozone-containing gas.

According to a further feature of the present invention, the transferring is performed through an ozone generator so as to further increase a proportion of ozone in the ozone-containing gas.

According to a further feature of the present invention, gas is also transferred from the second treatment chamber to the first treatment chamber through a catalytic filter.

According to a further feature of the present invention, pressure-waves are also generated within the first treatment chamber so as to enhance effectiveness of the ozone treatment.

According to a further feature of the present invention, prior to the treatment, at least a surface layer of the product is cooled sufficiently to cause condensation of ozone-containing water vapor on the surface layer.

According to a further feature of the present invention, prior to the treatment, at least a surface layer of the product is cooled sufficiently to cause freezing of ozone-containing water vapor on the surface layer.

According to a further feature of the present invention, the first and second treatment chambers share a common dividing wall which features at least one ozone generator and at least one catalytic filter.

According to a further feature of the present invention, the at least one ozone generator has an inlet switchably communicating with either the first or the second treatment chamber and an outlet switchably communicating with either the first or the second treatment chamber.

According to a further feature of the present invention, the at least one catalytic filter has an inlet switchably communicating with either the first or the second treatment chamber and an outlet switchably communicating with either the first or the second treatment chamber.

There is also provided according to the teachings of the present invention, a high concentration frame-type ozone generator comprising: (a) a plurality of elongated electrodes deployed in substantially parallel, spaced relation to each other so as to form a substantially flat electrode array; (b) a casing substantially enclosing the electrode array, the casing having an inlet and an outlet; and (c) a flow system associated with the casing configured to generate: (i) a recirculating flow of gas within the casing recirculating through the electrode array, and (ii) a through-flow of gas in through the inlet and out through the outlet, the through-flow having a volumetric flow rate significantly less than a volumetric flow rate of the recirculation flow.

According to a further feature of the present invention, the volumetric flow rate of the recirculation flow is at least ten times greater than the volumetric flow rate of the through-flow.

According to a further feature of the present invention, there is also provided a cooling system associated with the casing for cooling the casing.

According to a further feature of the present invention, there is also provided at least one additional electrode array similar to, and deployed parallel to, the electrode array such that the recirculation flow passes sequentially through the electrode array and the additional electrode array.

BRIEF DESCRIPTION OF THE DRAWINGS

The invention is herein described, by way of example only, with reference to the accompanying drawings, wherein:

FIGS. 26a–26e illustrate some typical electrode cross section shapes to be used in said ozonator.

FIG. 44 is a longitudinal cross-sectional view through a high concentration frame-type ozone generator, constructed and operative according to the teachings of the present invention.

FIG. 45 is a transverse cross-sectional view taken along the line IV—IV of FIG. 44.

DESCRIPTION OF THE PREFERRED EMBODIMENTS

The present application relates to a number of developments to do with systems for ozone treatment, and ozone generators for such systems.

The principles and operation of developments according to the present invention may be better understood with reference to the drawings and the accompanying description.

Specifically, a number of systems for ozone treatment of objects will be described with particular reference to FIGS. 1–23. Then, with reference to FIGS. 24–45, various structures of ozone generator and their applications will be described. It should be appreciated that the ozone generators of FIGS. 24–45 may be employed to advantage within the systems of FIGS. 1–23. The systems are not. however, limited to use of such ozone generators except where specified.

Figure 1:
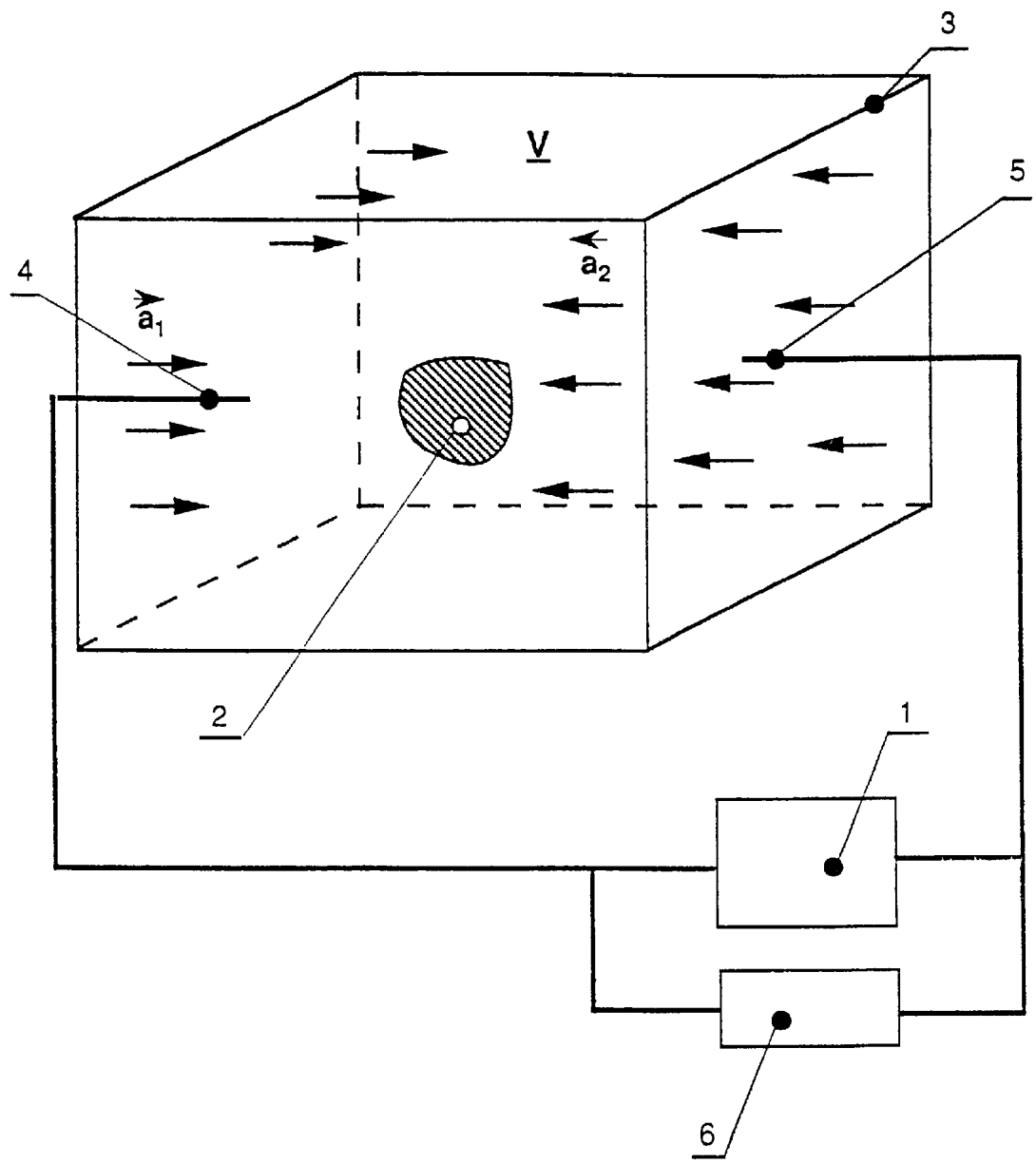
FIG. 1 illustrates schematically a treatment process of an object using an ozone-containing gas mixture.

Referring now to the drawings, FIG. 1 illustrates a treatment process of an object by a forced linear flow of an ozone-containing gas mixture, which alternately changes its direction. Such a system is in particular suitable for disinfection of objects with smooth curved surfaces, and without pores, such as agricultural produce of certain kinds (e.g. tomatoes; grapes and squashes in bulk, eggs, etc.).

Details of the system are as follows:

a device (1) for producing an ozone-containing gas mixture, maintaining gas circulation in the system;

the treated object (2);

borders (3) of the treatment space;

inlet (4) and outlet (5)—alternating for the gas mixture:

a device (6) for control of relative humidity and temperature of the gas mixture in the treatment space, a flow vector ($a_1$) in one direction, and;

a flow vector ($a_2$) in the opposite direction.

The gas flowing within the system by re-circulation is driven by a fan located in the device for providing the gas mixture (see item 1, above), enters through inlet-outlet (4–5) into the treatment space (3), and reacts with the treated object (2) on one side and then on its other side, alternately, and then exits through inlet-outlet (4–5), when the flow direction changes. While passing towards the treatment space, the gas flows through the humidity and temperature controls (6).

Figure 2:
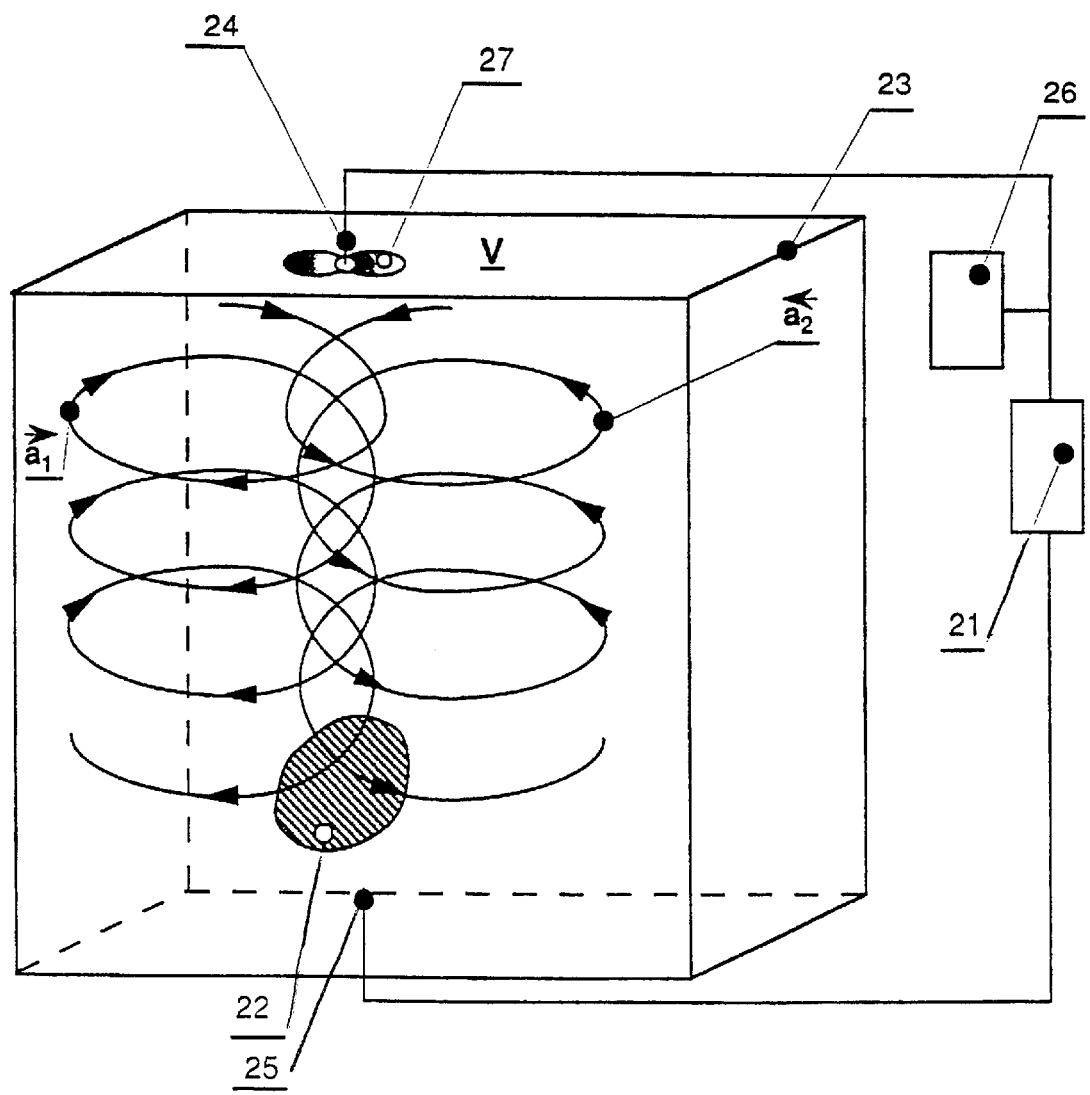
FIG. 2 illustrates schematically a variation of the process as shown in FIG. 1.

FIG. 2, illustrates a treatment process of an object by forced spiral conical flow of an ozone-containing gas mixture, which changes its direction alternately. In this system objects having different geometric shapes can be treated, provided that their surface areas are smooth and without pores. The flow in a spiral motion is accomplished by a fan-like gas mixer. The alternate direction of flow concomitant with a spiral motion ensure a uniform treatment of the objects to be treated, as long as the treatment intervals in the different directions are equal.

The details of this system are as follows:

device for producing an ozone and gas mixture (21);

the treated object (22);

the borders (23) of the treatment space;

inlet-outlet (24–25) (alternately);

controls (26) for humidity and temperature in the gas mixture.

The changes in the flow direction within the treatment space is accomplished by changing the direction of the gas mixer. A uniform treatment can also be achieved by rotating the treated objects without changing the direction of the gas flow.

Figure 3:
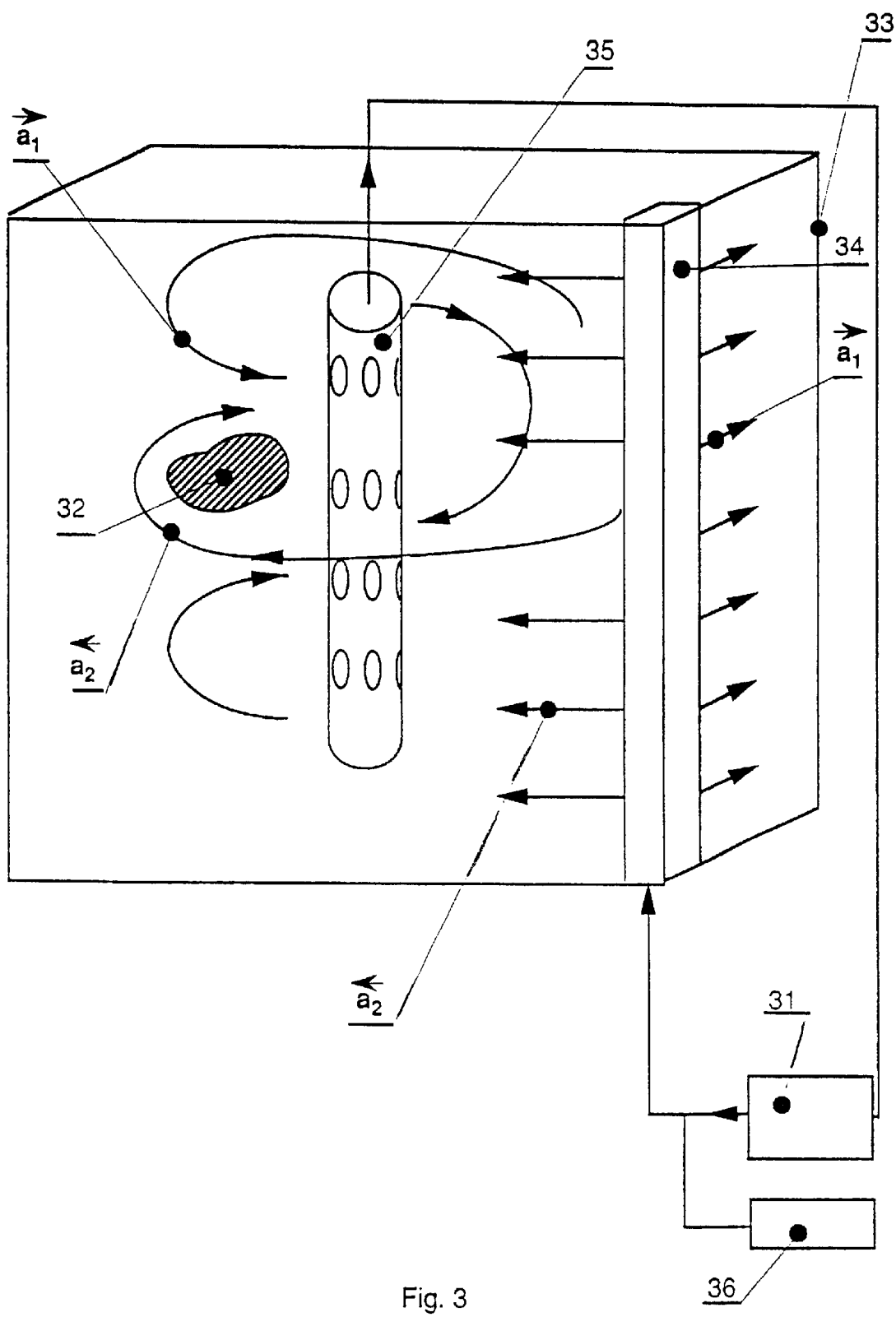
FIG. 3 illustrates a spiral cylindrical flow of a gas mixture, which alternately changes its direction.

FIG. 3, illustrates a spiral cylindrical flow of a gas mixture, which changes its direction alternately. The best results with such a system are obtained with smooth objects having different shapes when placed in layers, and the layers are placed on screens. The above gas flow is produced by driving the gas mixture in a tangential direction and its outflow from the center of the treatment space.

The details of the system are:

a device (31) for producing an ozone and gas mixture;

the treated object (32);

the borders (33) of the treatment space;

the gas inlet (34) that changes the direction of the entering gas by a 900 angle, to achieve a tangential velocity that alternately changes its direction;

the exhaust outlet for gas (35), which is cylindrical and perforated, and located at the center of the treatment space, is responsible for creating a cylindrical spiral motion in parallel ($a_2$);

controls (36) for gas humidity and temperature 36.

Figure 4:
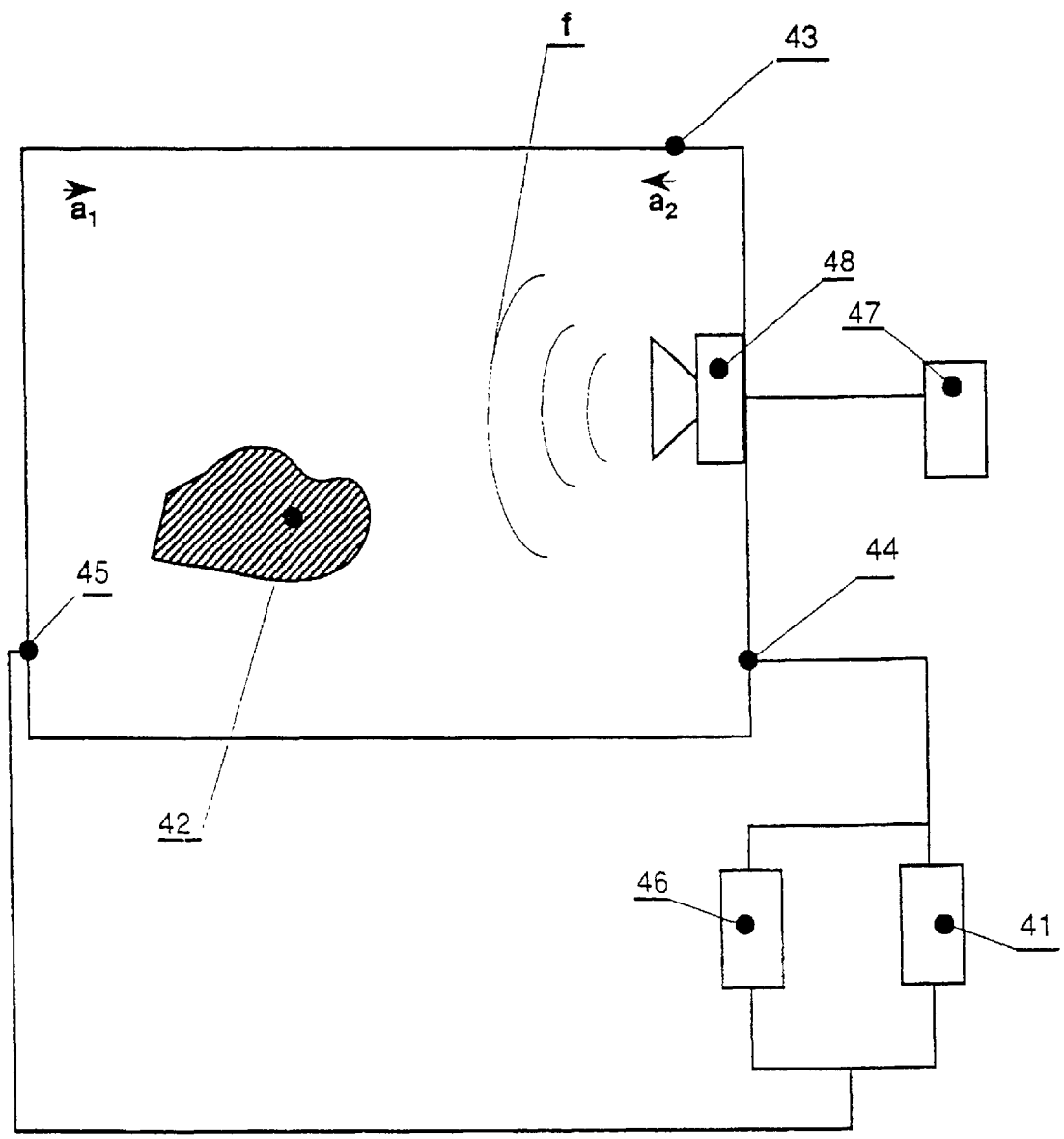
FIG. 4 illustrates the treatment process of an object as shown in FIG. 2. combined with acoustic waves.

FIG. 4, illustrates a treatment process of an object by forced flow of an ozone-containing gas mixture, combined with acoustic waves. The gas flow in the treatment space can be effected in all of the above ways (FIGS. 1, 2 and 3). The acoustic waves are produced by operating an acoustic transducer (such as an ordinary loudspeaker), which ensures the ozone transport to regions where the gas is kept stagnant, such as the porous surface of certain products and objects with various corners. The gas mixture reaching such regions facilitates their disinfection and purification.

The details of the system are:

a device (41) for producing an ozone and gas mixture;

the treated object (42);

the treatment space (43);

gas inlet-outlet (44–45);

gas humidity and temperature controls (46):

an electronic device for producing acoustic waves (47), and an acoustic transducer (48).

When the ozone-containing gas flows into the treatment space (43) the treated object (42) is disinfected. The acoustic waves (f) are produced by the transducer 48 and they interact with the borders of the treatment space and the treated object, and when the frequency and amplitude of the acoustic waves are changed the gas mixture flows in different directions. Such a flow cannot take place without the acoustic waves. In addition, this gas flow brings about better and more uniform treatment of all objects, including those with porous surfaces.

Figure 5:
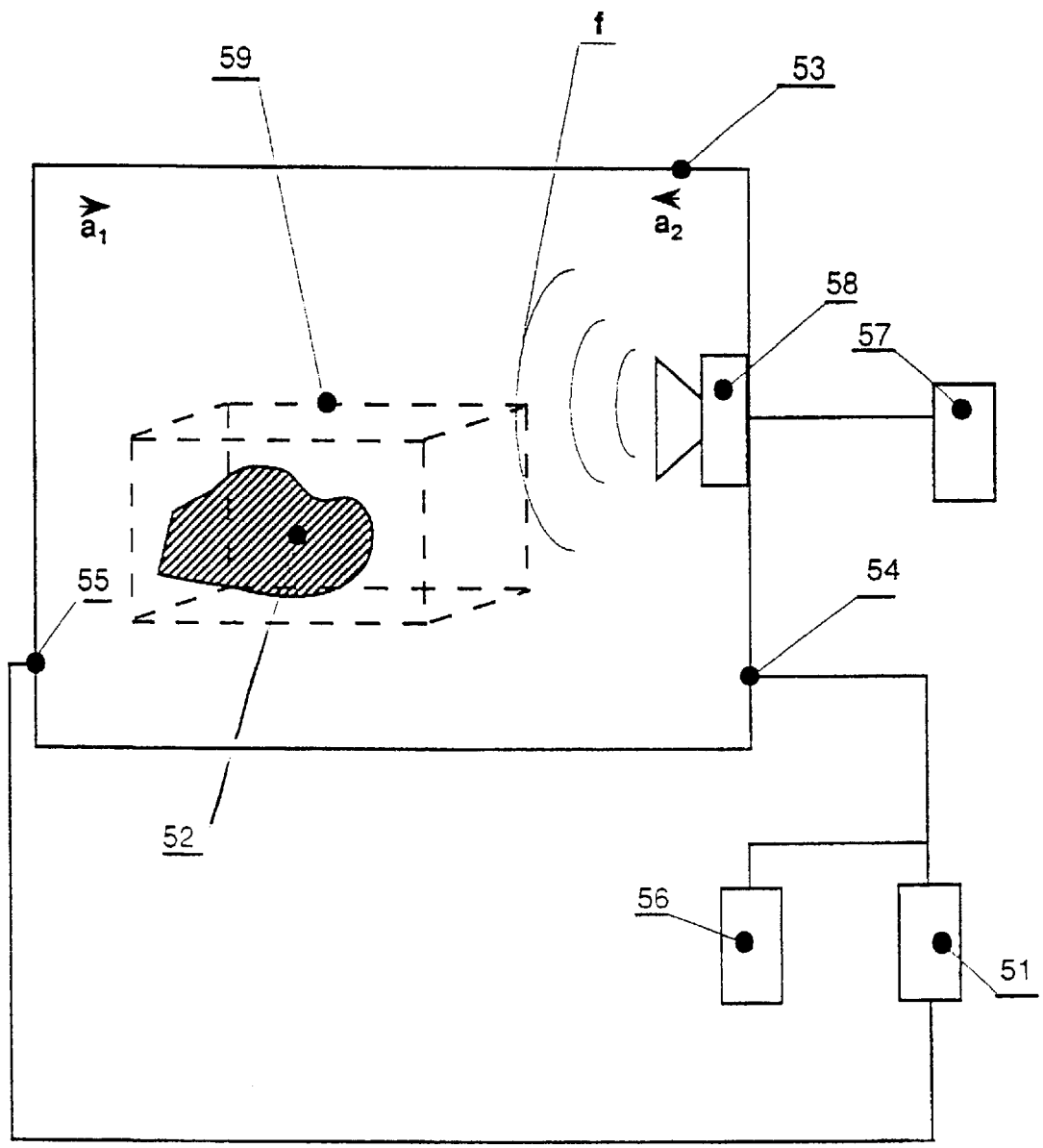
FIG. 5 illustrates a treatment process of objects in a package with openings.

FIG. 5, illustrates a treatment process of an object in a package with openings, which enable an ozone-containing gas mixture to come in contact with the packaged objects.

The details of the system are as follows:

a device for producing a homogeneous ozone and gas mixture (51);

the treated object (52);

the treatment space (53);

the gas inlet-outlet (54–55);

controls (56) for the gas mixture temperature and relative humidity;

an electronic device (57) for operating the acoustic transducer;

the acoustic transducer (58);

package (59) of the treated object.

In this particular case, the interaction of acoustic waves (1), when a change in their amplitude and frequency occurs with the treated objects, their package and the borders of the treatment space, the ozone-containing gas mixture enters through openings in the package more easily, thus disinfecting and purifying the surfaces of the treated objects.

Figure 6:
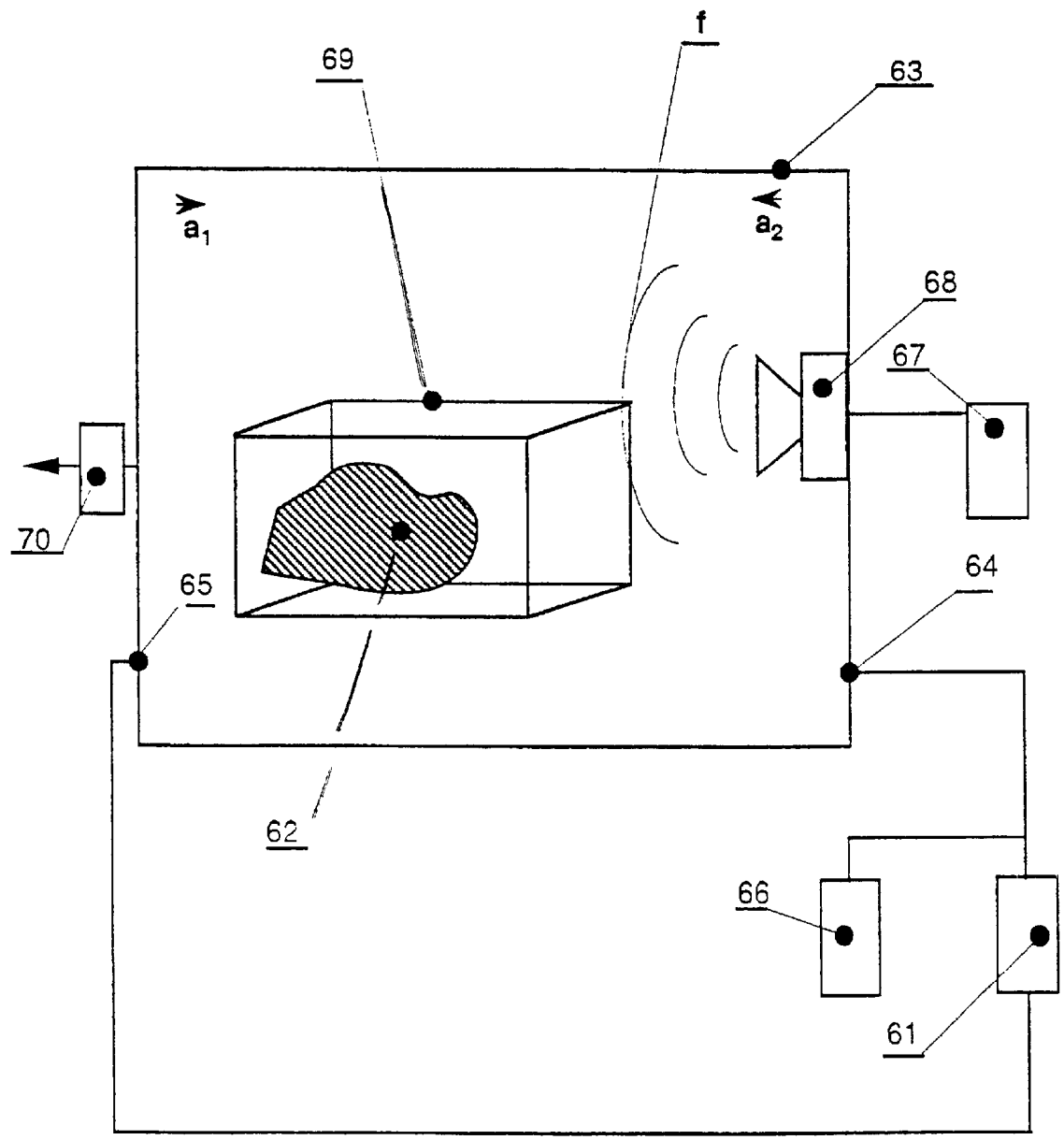
FIG. 6 illustrates a variation of FIG. 5.

FIG. 6, illustrates a treatment process of an object in a porous package. A porous material such as a micronic filter, which facilitates a long-term storage of objects that underwent disinfection or purification by ozone.

The details of the system are as follows:

a device (61) for producing a homogeneous ozone and gas mixture;

the treated object (62);

the treatment space (63);

the gas inlet-outlet (64–6~5);

controls (66) for the gas mixture temperature and relative humidity;

an electronic device (67) for operating the acoustic transducer;

the acoustic transducer (68);

a porous non-collapsible package (69) of the treated object;

a vacuum pump 70.

The vacuum pump drives the homogeneous gas mixture through the treatment space (63), thus disinfecting the treated object (62).

Figure 7:
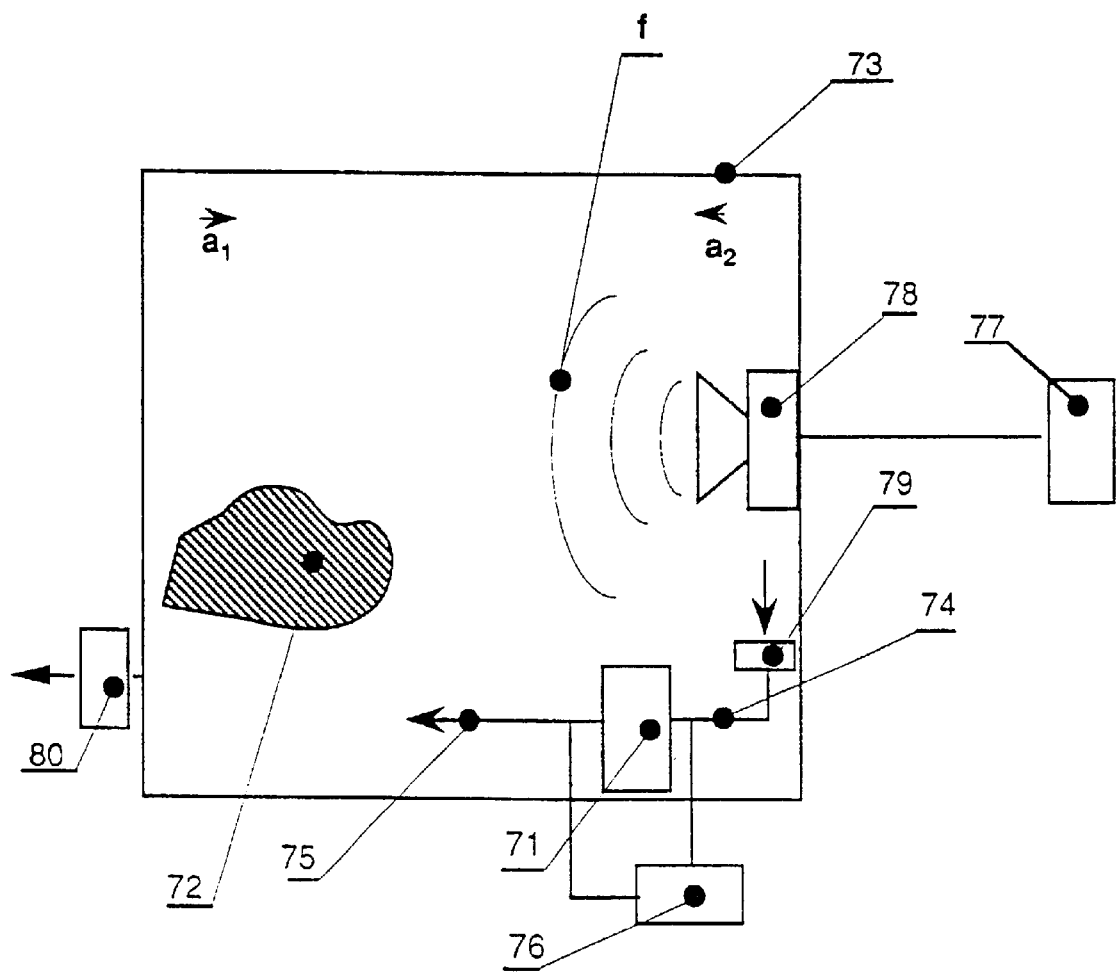
FIG. 7 illustrates a treatment process of an object with a system for achieving a homogeneous mixture of ozone and a carrier gas in the treatment space.

FIG. 7, illustrates a treatment process of an object with a system for achieving a homogeneous mixture of ozone and a carrier gas in the treatment space. This system is intended to operate a device for producing a homogeneous ozone-containing gas mixture, based on a frame-type ozone generator, described below. This ozone generator produces ozone in a homogeneous mixture with a carrier gas, which does not necessitate a dedicated blower (fan).

The details of the system are as follows:

a frame-type ozone generator (71);

the treated object (72);

the treatment space (73);

the gas inlet-outlet (74–7~5);

the controls (76) for the gas mixture temperature and humidity;

an electronic device (77) for operating the acoustic transducer;

the acoustic transducer (78);

a catalytic filter (79) at the inlet of the ozone generator, in order to avoid gradual increase in the ozone concentration with time.

When a frame-type ozone generator is installed within the treatment space, the ozone concentration can be controlled by an interaction between the acoustic wave frequencies and the frequency of the power supply of the ozone generator. Synchronous and asynchronous states between the respective frequencies influence the ozone concentration in different ways, by modulating the duration of the gas mixture presence within the ozone generator.

Figure 8:
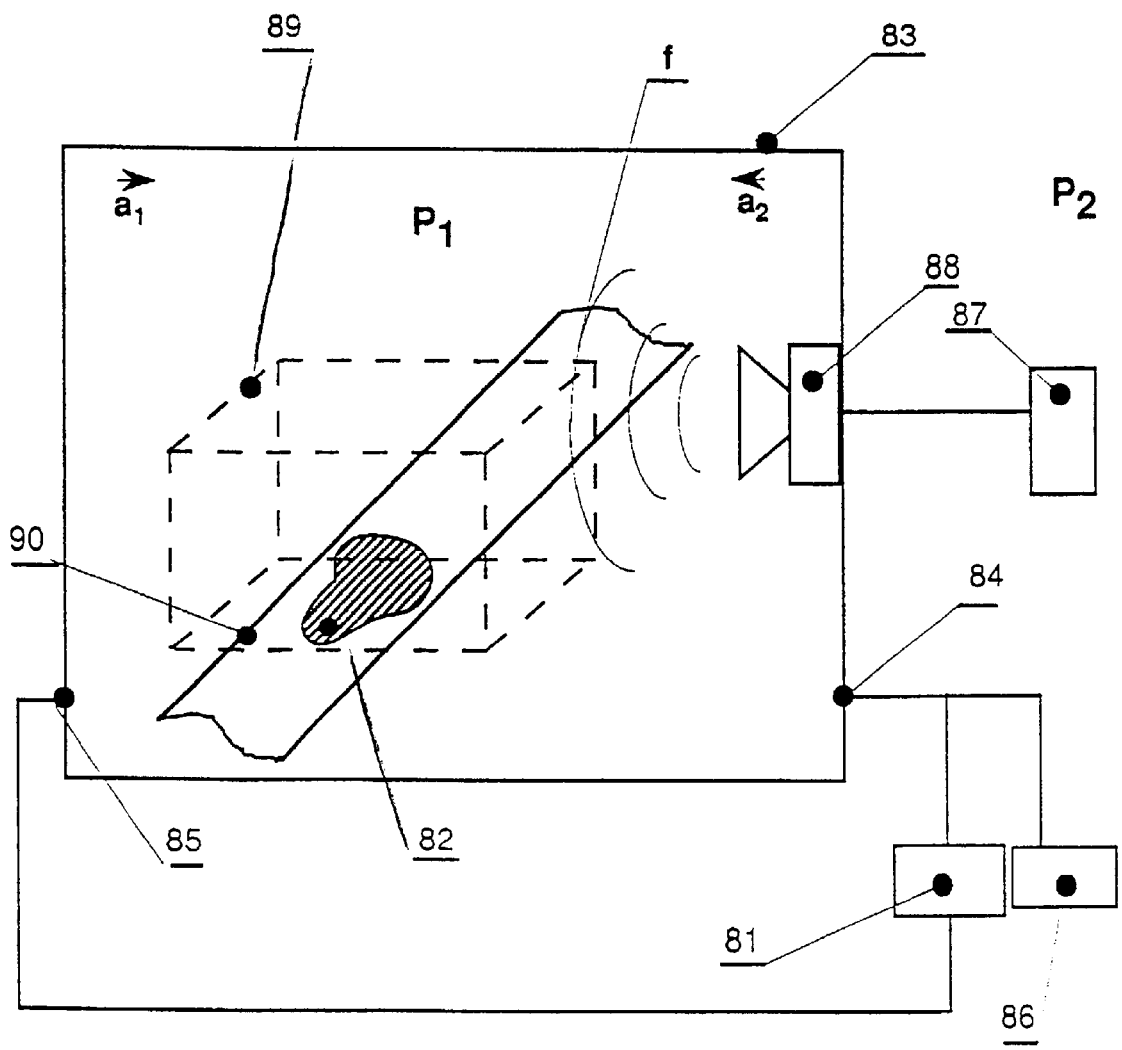
FIG. 8 illustrates a treatment process for a continuous operation.

FIG. 8, illustrates a treatment process for continuous operation on a moving belt. This system is intended for a continuous disinfection and purification of objects carried along moving belts of different kinds while maintaining negative pressure in the treatment space, thus preventing the escape of ozone from the treatment space or from the both ends of the moving belt.

The details of the system are as follows:

a device (81) for producing a homogeneous ozone and gas mixture, the treated object (82);

the treatment space (83);

the gas inlet-outlet (84–85);

the controls (86) for the gas mixture temperature and humidity;

an electronic device (87) for operating the acoustic transducer 87;

the acoustic transducer (88);

a moving belt (89);

internal negative pressure (pi);

external pressure (P2).

Figure 9:
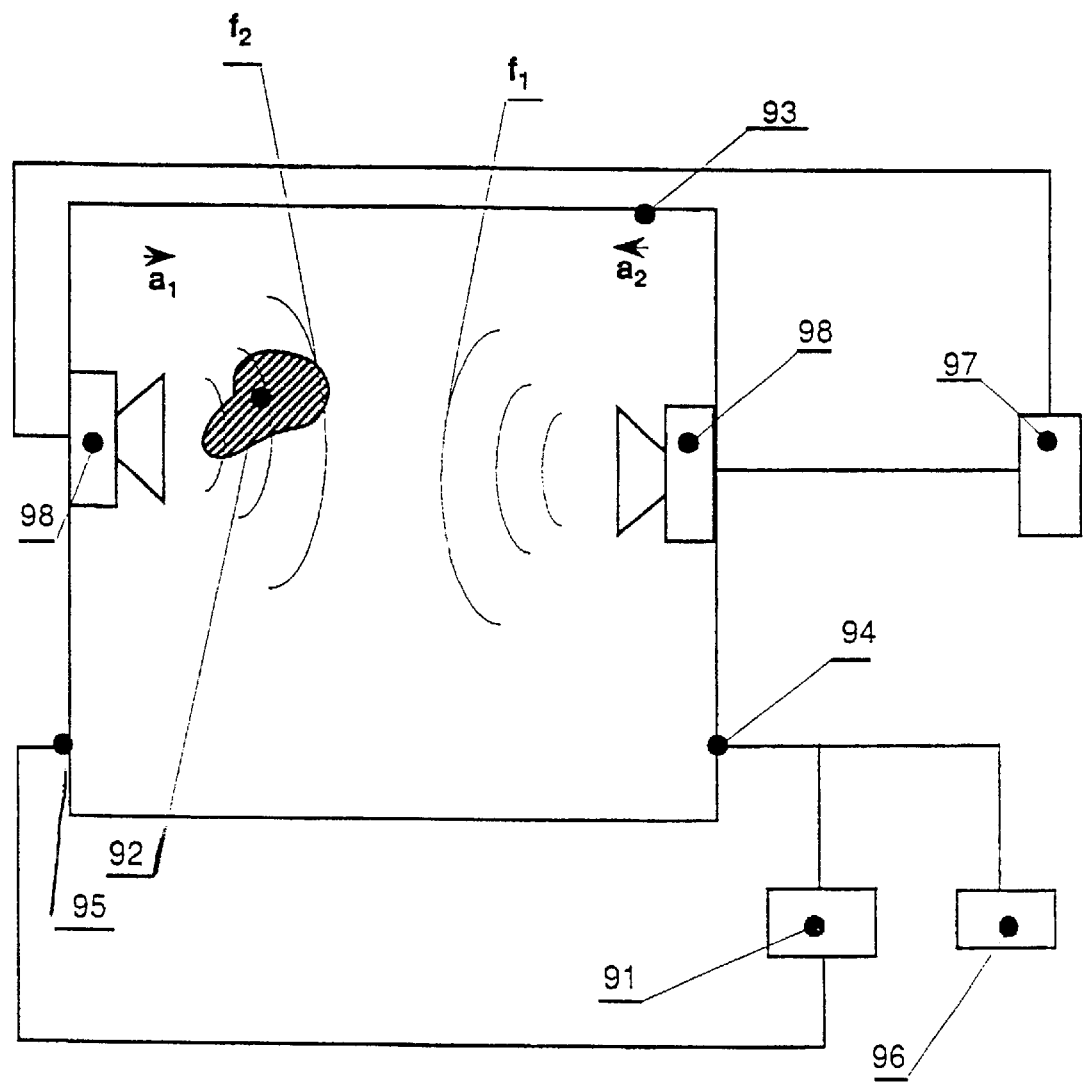
FIG. 9 illustrates the treatment process as in FIG. 4 wherein said acoustic waves are produced by transducers.

FIG. 9, illustrates a treatment process with two transducers. in order to produce acoustic waves, with interaction between them. Such an interaction is accomplished by collision of acoustic waves from different sources, which causes effective dispersion of the gas mixture in all directions. In this system disinfection and purification take place in the entire surface area and uniformly. In this manner the penetration of the gas mixture into the pores of the porous surfaces is much better than in ordinary systems.

The details of the system are as follows:

a device (91) for producing a homogeneous ozone and gas mixture.

the treated object (92);

the treatment space (93);

the gas inlet-outlet (94–9–5);

the controls (96) for the gas mixture temperature and humidity;

an electronic device (97) for operating the acoustic transducer;

the acoustic transducer (98);

acoustic waves, with interaction between them (f1) and (f2).

Figure 10:
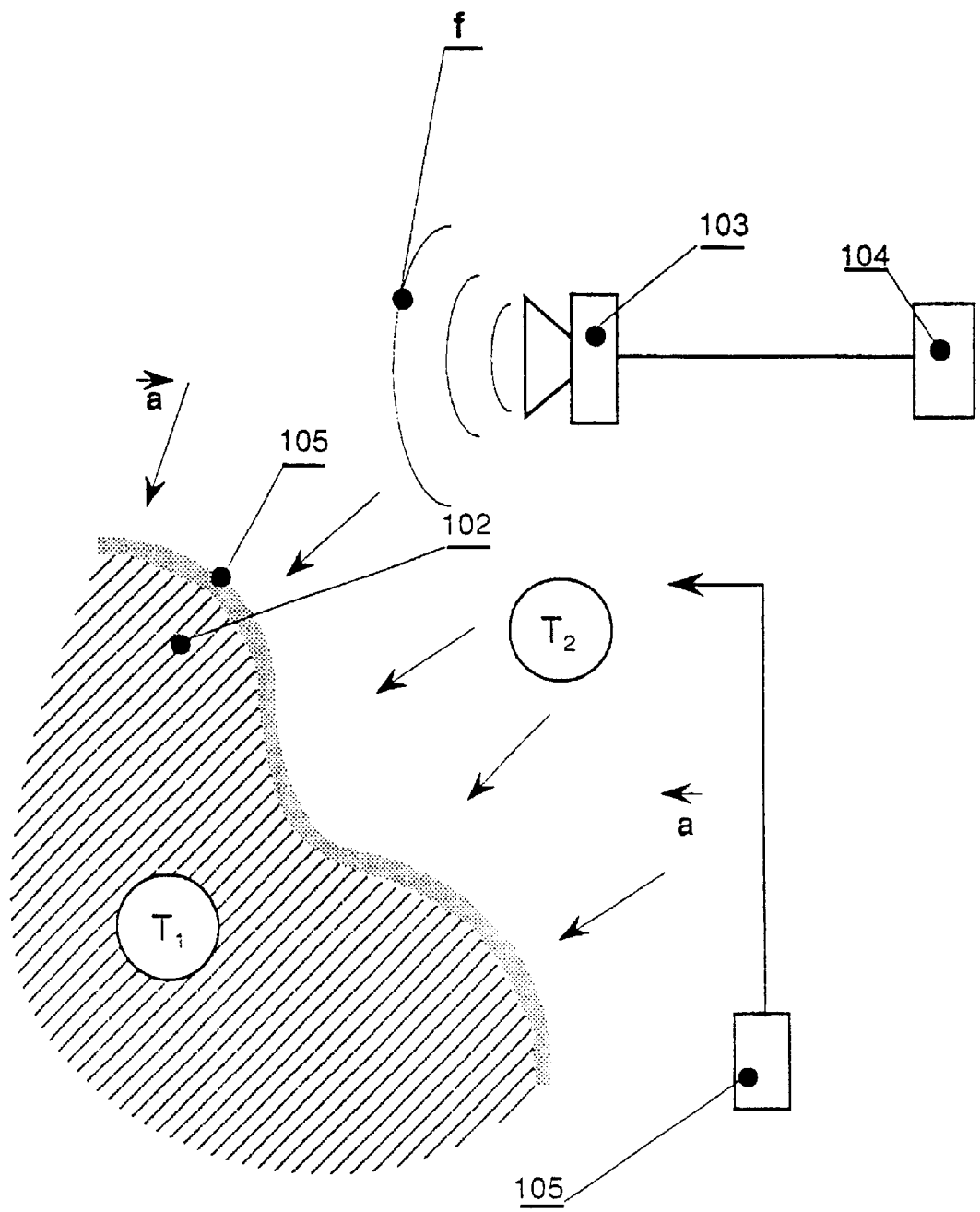
FIG. 10 illustrates a treatment process of an object by the transport of ozone obtained through phase transition of water vapors.

FIG. 10. illustrates a treatment process of an object by transport of ozone, obtained through phase transition of water vapor. Such a process occurs when the temperature of the treated objects (e.g. fruits, vegetables, meat) is:

(a) chilled to a temperature at which contact with the gas mixture brings about coating of the treated objects with a layer of water containing dissolved ozone, and this layer causes an effective disinfection of the treated objects' surfaces, or (b) chilled to a temperature below the water freezing point, when an ice layer containing ozone is formed on the surface of the treated objects.

In case (a), the dew point front may form before the gas mixture reaches the surface of the treated objects. This may happen when the temperature of the treated objects is far below the dew point of the gas mixture. As a result, the temperature gradient between the treated objects and the gas mixture leads to the formation of ozone-containing fog, which acts as a very efficient disinfection medium.

In case (b), ozone-containing frost may form on the outer surface of the treated objects. In both cases the ozone treatment is highly effective, especially in combination with alternating flow direction vectors of the gas mixture, and with the acoustic waves interacting with the surfaces of the treated objects and, when applicable, also with their package and the treatment space borders.

The details of the system are as follows:

a device (101) for producing a homogeneous ozone and gas mixture:

the treated object (102);

the acoustic transducer (103);

an electronic device (104) for operating the acoustic transducer;

the coating layer (105) on the surface areas of the treated objects, the temperature (T1) of the treated objects;

the temperature (T2) of the gas mixture;

the direction (a) of the gas flow vector;

the acoustic waves (f).

Figure 11:
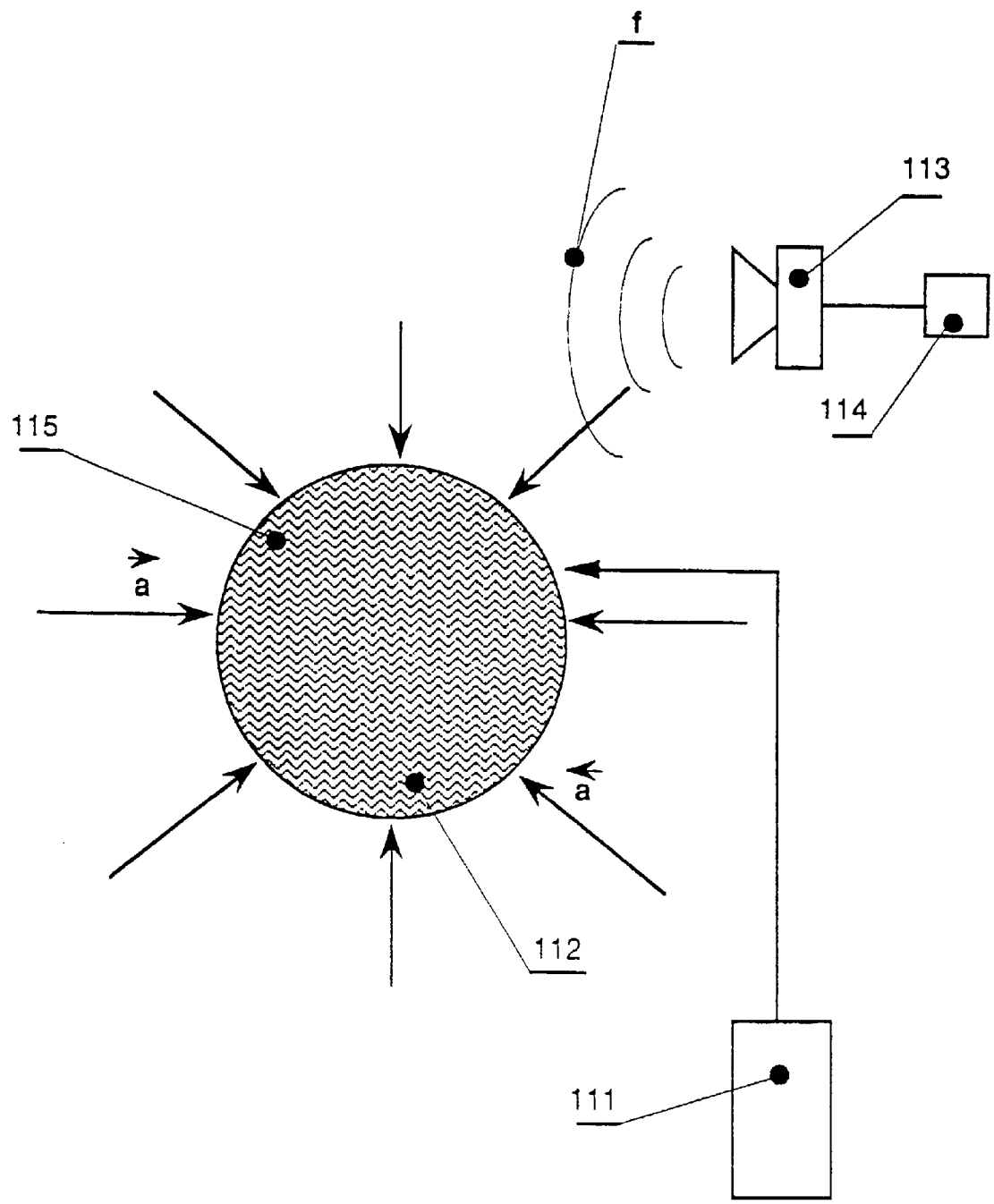
FIG. 11 illustrates a treatment process of a liquid droplet with an ozone-containing gas mixture.

FIG. 11, illustrates the treatment process of water (or another liquid) droplet with an ozone-containing gas mixture. This process takes place when the liquid droplets come in contract with a homogeneous ozone-containing gas mixture, for a time interval sufficient to enable permeation of the ozone present in the gas mixture into the droplets. In this case the acoustic waves greatly increase the ozone permeation rate into the droplets.

Also, in this case the disinfection and purification of liquids by ozone is very efficient, and so is their deodorization as well. This process is different from the conventional method for the production of an ozone solution, since the former is performed by atomization of the droplets in the presence of the gas mixture, whereas the conventional process is performed by bubbling the gas mixture into the liquid.

The details of the system are as follows:

a device (111) for producing a homogeneous ozone and gas mixture;

a droplet (112);

an acoustic transducer (113);

an electronic device (114) for operating the acoustic a treated droplet (115).

The droplets are surrounded by the gas mixture and ozone permeates into them, thus disinfecting, purifying and deodorizing the liquid. Generally, the smaller the droplet size the higher the efficacy of the process. In addition, when the ozone-containing gas mixture dissolves in the droplets, appreciable amounts of other dissolved gases are released, thereby enhancing the deodorization of the liquid being treated as a finely dispersed mist.

Figure 12:
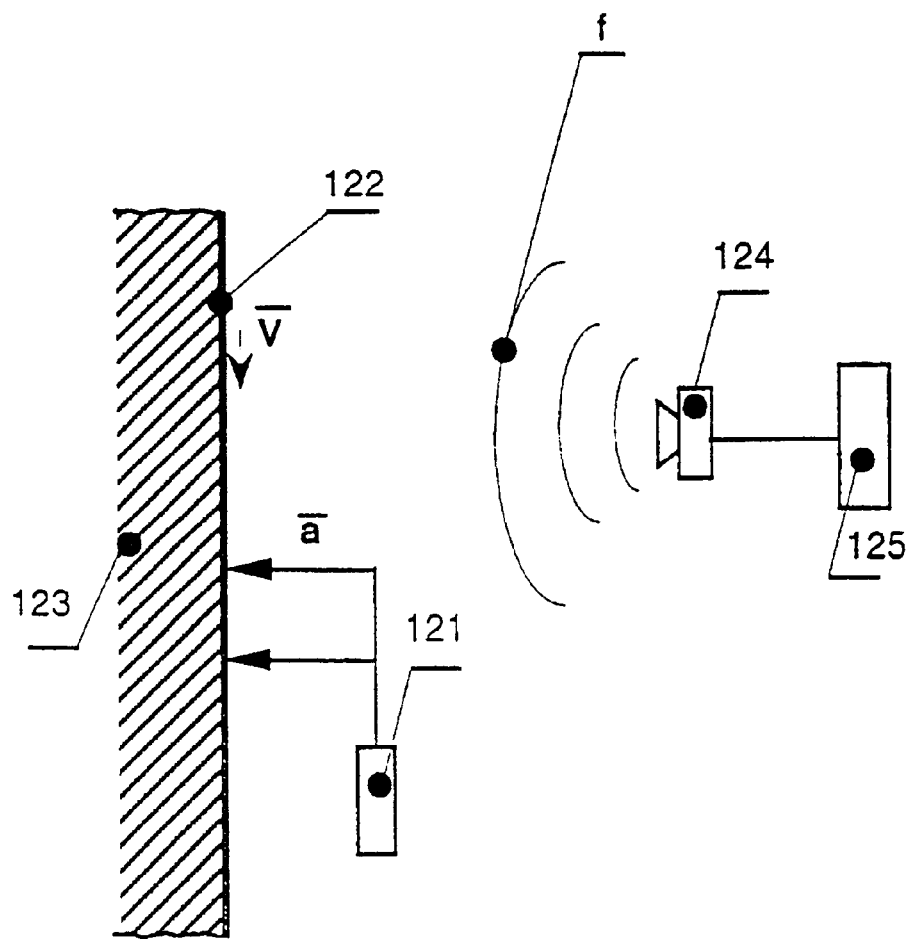
FIG. 12 illustrates a treatment process of a liquid falling film by an ozone-containing gas mixture.

FIG. 12, illustrates a treatment process of a liquid in a thin falling film by an ozone-containing gas mixture.

This process occurs when the gas mixture is passed over a thin falling film of a liquid undergoing disinfection, purification or deodorization. A thin film can be formed by allowing a liquid to fall on a solid surface having a suitable geometric shape. In this manner the operation mode affords a high treatment efficiency, due to the large surface area of the this falling film. The details of the system are as follows:

a device (121) for producing a homogeneous ozone and gas mixture;

a thin liquid (122);

a solid surface (123) on which the thin liquid film is formed 123;

an acoustic transducer (124);

an electronic device (125) for operating the acoustic transducer.

In addition to the disinfection, purification or deodorization of liquids, the surface on which the liquid falls, is also disinfected. The latter process can be very satisfactory for treating animal (including fish) carcasses or parts therefrom.

Figure 13:
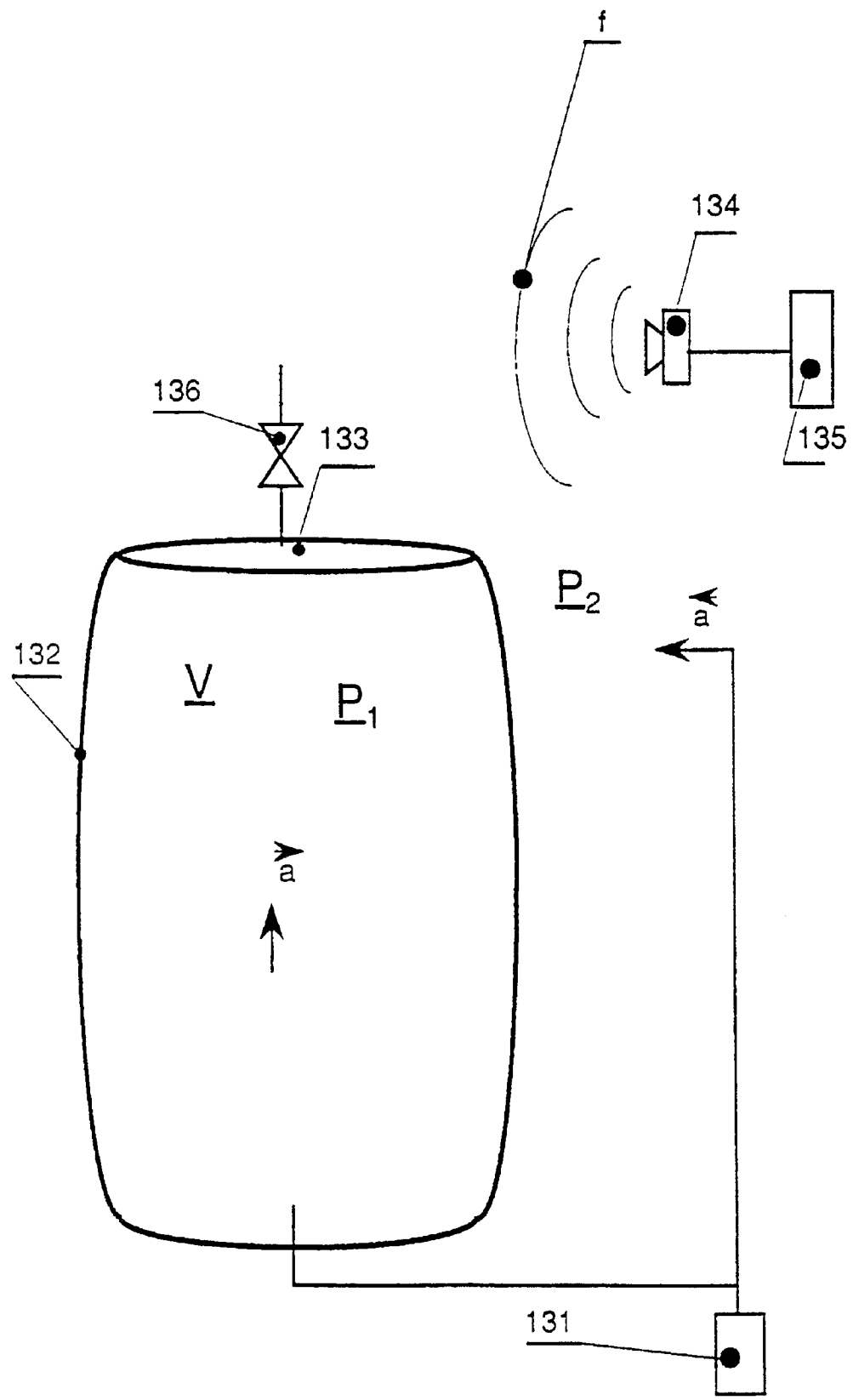
FIG. 13 illustrates a variation of FIG. 12, wherein said thin film is falling from a sliding tray.

FIG. 13, illustrates a treatment process for disinfection. purification or deodorization of a liquid in a thin film falling from a sliding tray. The ideal shape for such a tray is circular and that for the falling film is cylindrical. The gas mixture is introduced into this cylinder at a pressure sufficient to cause partial bulging of the cylinder, thereby forming a barrel-like body. Also in this case, the flow of the gas mixture inside and possibly also outside the "barrel", in combination with acoustic waves, improve the efficiency of the treatment.

The details of the system are as follows:

a device (131) for producing a homogeneous ozone and gas mixture;

a barrel-shaped falling film (132);

a sliding tray (133) with monotonous borders (except for the liquid detachment corner);

an acoustic transducer (134);

electronic device (135) for operating the acoustic transducer;

a valve (136) for creating pressure inside the "barrel";

the internal volume (v) of the "barrel";

the internal pressure (Pi) of the "barrel;

the direction (a or a') of the gas mixture flow;

acoustic waves (f).

Figure 14:
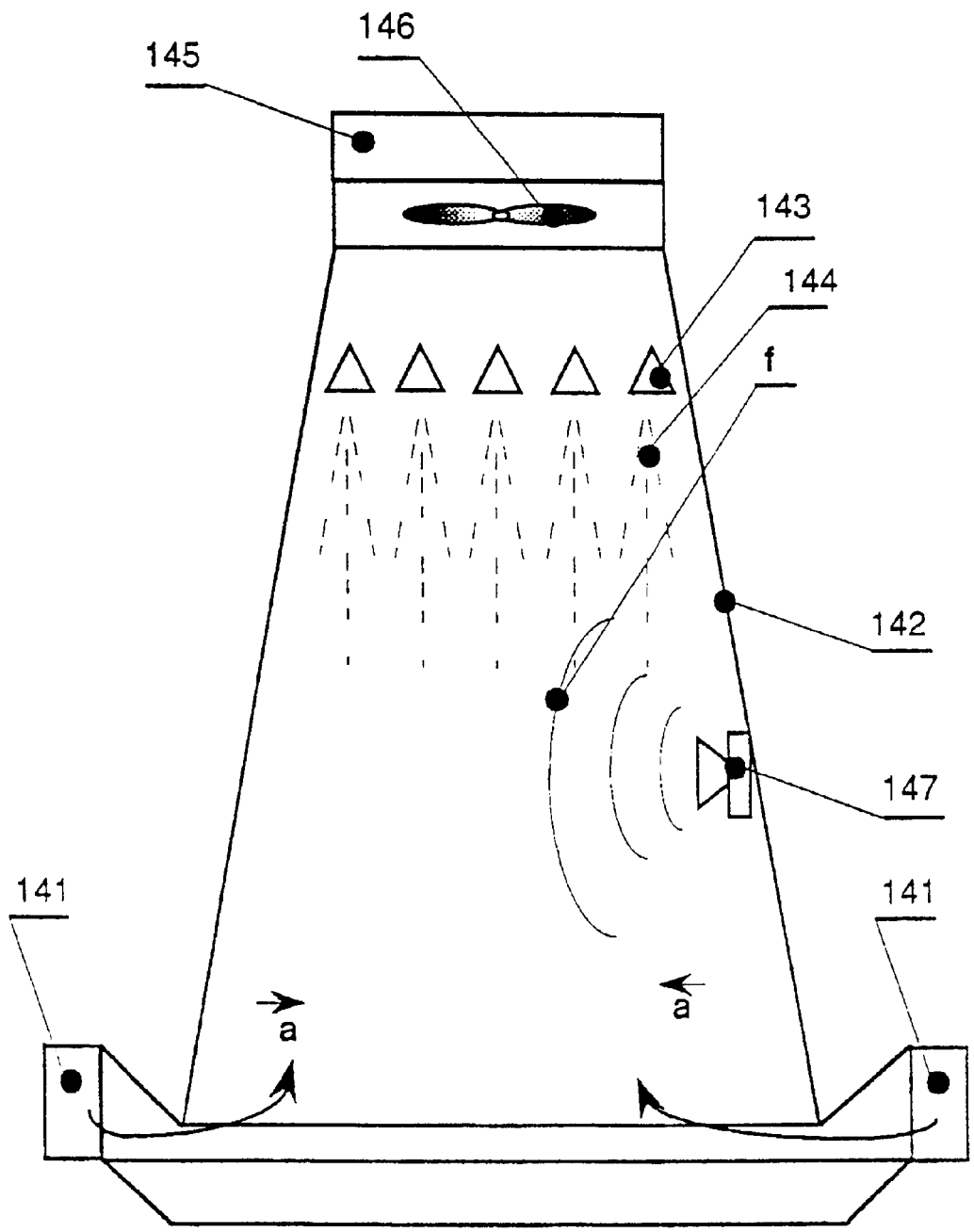
FIG. 14 illustrates a treatment process of a liquid spray with an ozone-containing gas mixture.

FIG. 14, illustrates a biphasic treatment process of water with an ozone-containing gas mixture. This treatment is carried out in a tower, resembling a cooling tower. Water is sprayed by fine sprinklers, creating an aerosol. The gas mixture is driven from the bottom of the tower, which is in the opposite direction of the falling aerosol. The gas mixture surrounds the aerosol and disinfects, purifies and deodorizes the aerosol. This system is intended for use on the cooling water in cooling towers and also for treating relatively small water bodies, such as swimming pools and drinking water reservoirs.

The details of the system are as follows:

a device (141) for producing a homogeneous ozone and gas mixture:

a tower (142);

a sprinkler (143);

an aerosol (144);

a catalytic filter (145);

a blower for small towers (146);

an acoustic transducer (147);

the direction of the gas mixture flow (a or a'), and acoustic waves (f).

Figure 15:
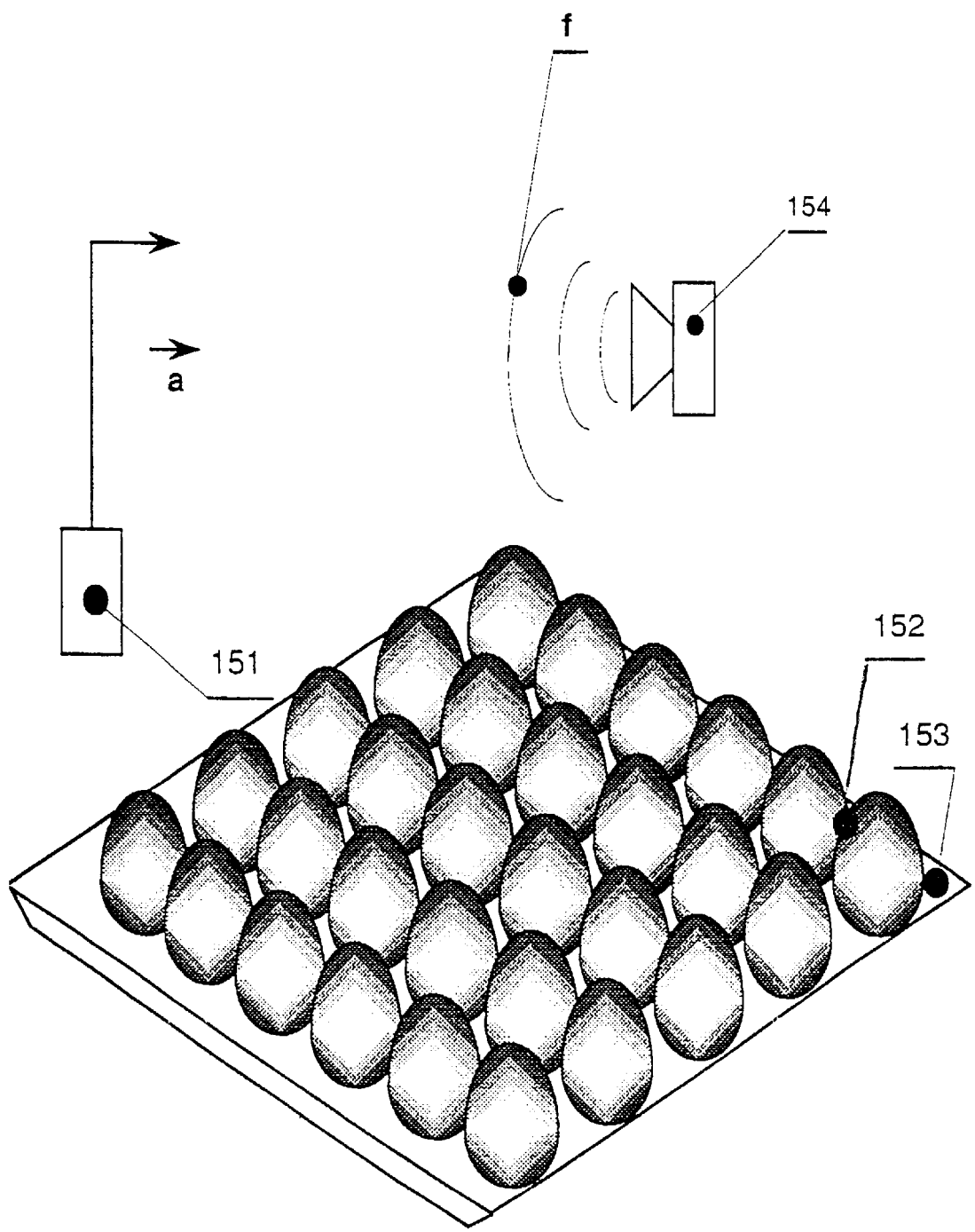
FIG. 15 illustrates a treatment process of eggs.

FIG. 15, illustrates a treatment process of eggs arranged on an open tray with an ozone-containing gas mixture. The object of this treatment is for disinfecting the shells of edible or hatching eggs, by passing the gas mixture around the external surfaces of the eggs. Most of the egg surface area is exposed to said gas mixture with a very small surface touching the trays. The disinfection efficiency can be greatly improved by acoustic waves, which enhance the penetration of ozone into the space between the eggs and the trays on which they. are loaded, as well as into the pores of the egg shell. By limiting the treatment period, the disinfection process can be limited to the egg shells only.

The details of the system are as follows:

a device (151) for producing a homogeneous ozone and gas mixture;

treated eggs (152);

a tray (153);

acoustic transducer (154).

Figure 16:
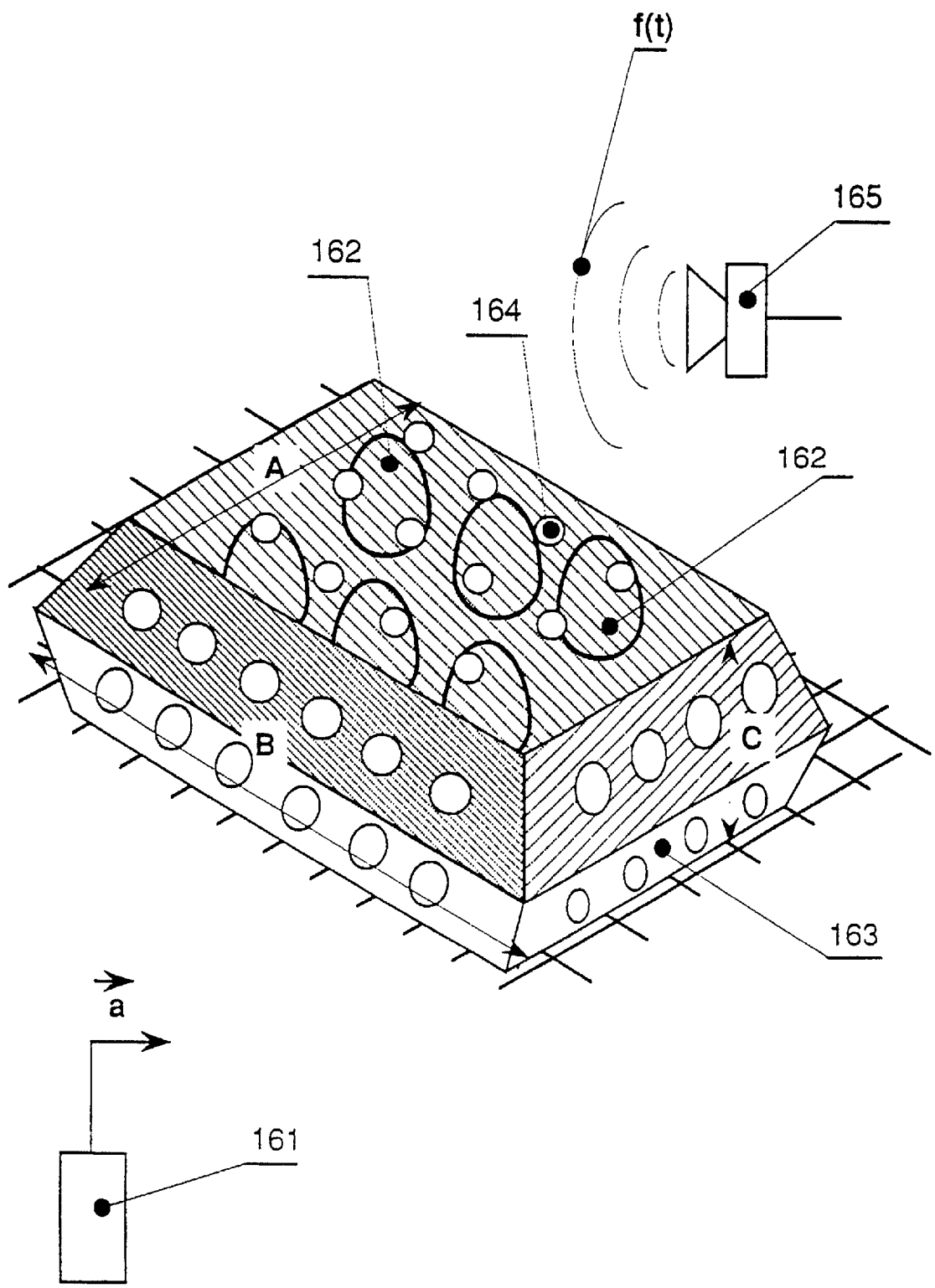
FIG. 16 illustrates a variation of FIG. 15.

FIG. 16, illustrates a pretreatment process of eggs in a package using an ozone-containing gas mixture. This application enables to disinfect the egg shells placed in boxes with openings, thus permitting the flow of the gas mixture into them. In this case also, the disinfection efficiency can be greatly improved by acoustic waves that interact with the box walls, thus enhancing a rapid penetration of ozone into the spaces between the eggs and the boxes in which they are packed, as well as into the egg shell pores. This mode of operation facilitates the disinfection of the egg shells only when this is desired.

The details of the system are as follows:

a device (161) for producing a homogeneous ozone and gas mixture;

the treated eggs (162);

a box (package), (163);

opening (164) in the box;

acoustic transducer (163), and the dimensions of the box (A, B and C).

This application also makes it suitable for treating similarly packed agricultural produce, such as fruits and vegetables.

Figure 17:
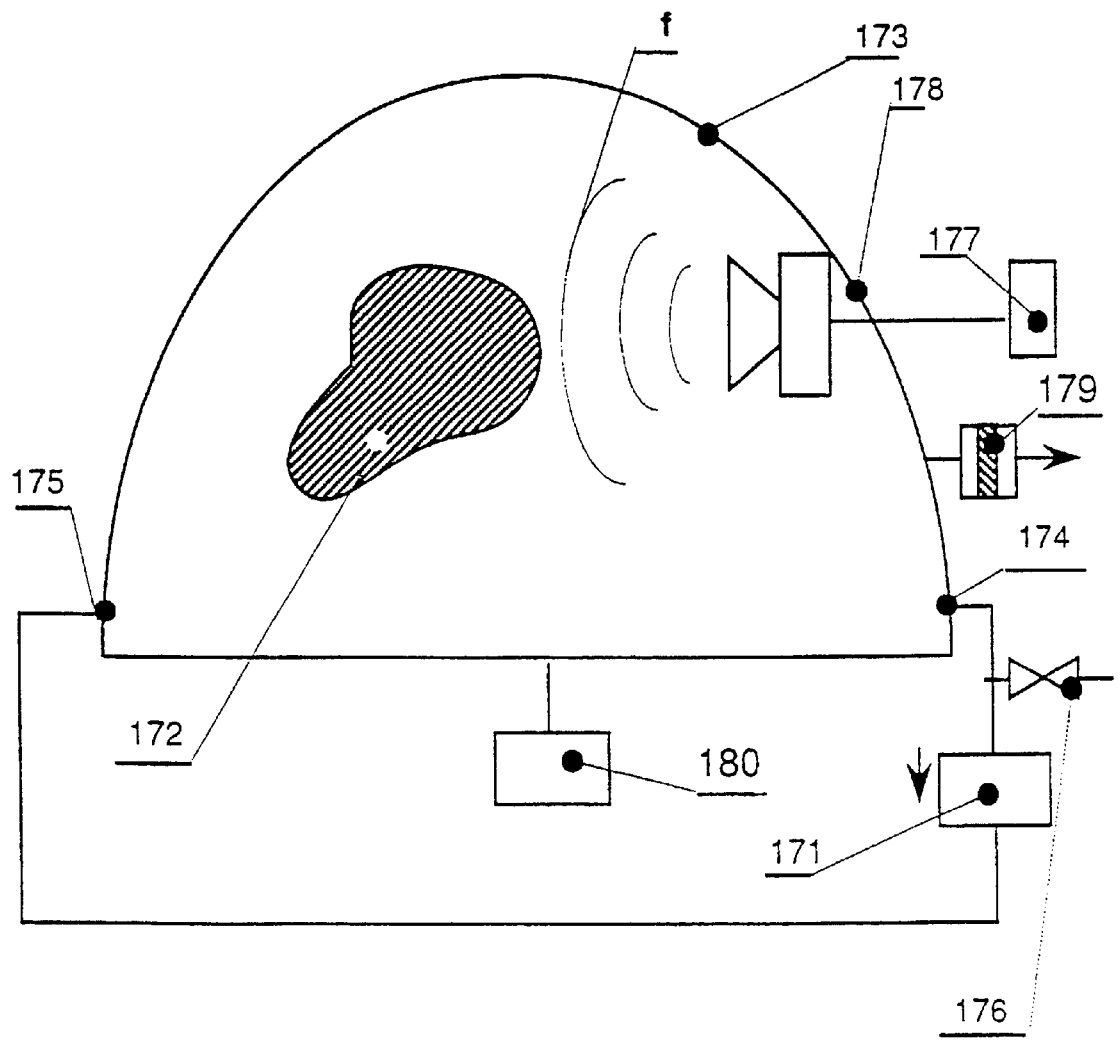
FIG. 17 illustrates a system for disinfecting within the treatment space, constructed by inflating a film wrapped around an object to be treated.

FIG. 17. illustrates a system for disinfecting within the treatment space. constructed by inflating a film wrapped around an object to be treated.

The details of the system, as shown in the above figure, are as follows:

A device (171) for producing a homogeneous ozone and gas mixture for treatment, inflation and recirculation.

The treated object (172).

The inflatable treatment space (173).

The inlet for the gas mixture (175.

The outlet for the gas mixture (174.

A control valve for external gas, for inflating the treatment space (176).

An electronic device for operating the acoustic transducer (177).

An acoustic transducer (178).

A gas release device and catalytic filter (179).

Control elements (180) for the gas mixture temperature and relative humidity.

As can be noticed, the system is characterized by its mobility and flexibility. permitting its folding and vacuum packing requiring a minimum packing volume. In this manner it can be used for treating single plants, such as trees and brushes, with pesticides, as well as for disinfecting of single objects such as medical appliances, laboratory equipment, etc.

Figure 18:
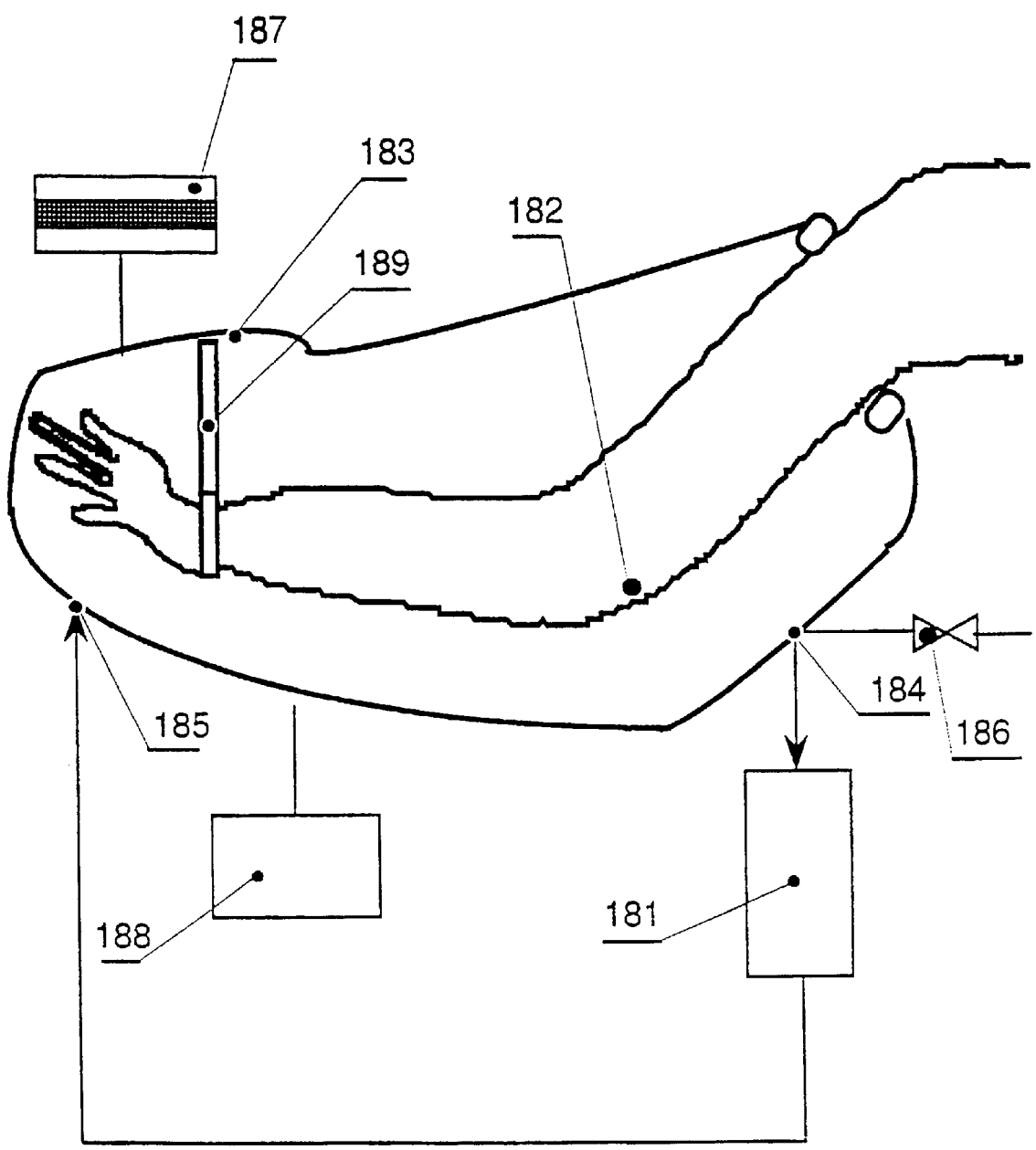
FIG. 18 illustrates a system for disinfecting of open wounds and burns before or/and after any medical treatment.

FIG. 18, illustrates a system for disinfecting of open wounds and burns before or/and after any medical treatment.

The details of the system are as follows:

A device (181) for producing a homogeneous mixture of ozone and gas for inflation and gas recirculation.

The treated object with burns or open wounds (182).

The gas outlet (184)

The gas inlet (185)

A control valve for external gas, for inflating the treatment space (187).

The control elements (188) for the gas mixture temperature and relative humidity.

A device (189), such as a ring-like holding cuffs and a strap to permit separation of the object from the film.

This system is intended for the isolation of areas in the treated area having open wounds, before or after any medical treatment, or burns. The treatment space may wrap the whole body, when the face is covered with a gas mask fitted with a catalytic filter, such as carbon.

Turning now to FIGS. 19–23, a system generally designated 190, constructed and operative according to the teachings of the present invention, for efficient batch treatment with ozone will be described.

Batch treatment with ozone is typically highly inefficient. Large amounts of energy are employed to generate sufficient ozone to be effective for treatment. Since, however, ozone may not be released into the atmosphere, all ozone remaining at the end of the treatment of each batch must normally be broken down by catalytic filters before the treatment chamber can be opened to remove the product under treatment. To address this problem, system 190 provides a number of chambers between which residual ozone is transferred at the end of each batch.

System 190 can be used in a wide range of applications including, but not limited to, food products such as eggs, vegetables, meat and fish, and other products such as medical supplies.

Turning now to the features of system 190 in more detail, system 190 is made up of at least two treatment chambers 191, 192 which are used alternately (or, in the case of more than two chambers, in sequence) for batch ozone treatment. Separating between chambers 191 and 192 is a partition 193 provided with ozone generators 194 and catalytic filters 180.

Each of ozone generators 194 and catalytic filters 195 has independently switchable inlet and outlet conduits such that it can operate in any one of four different modes: recirculation within chamber 191; recirculation within chamber 192; pumping from chamber 191 to chamber 192; and, pumping from chamber 192 to chamber 191. Switching of the inlets and outlets, as well as actuation of the catalytic filters, is controlled by timers or a computerized control system, as will be described below.

Each chamber has at least one hermetically sealed door 196, and preferably, doors 196 at opposite ends to facilitate efficient loading and unloading of the chamber. This arrangement also allows independent access from opposite sides to provide full separation between areas containing treated and untreated produce. In a preferred embodiment, each chamber also features an acoustic transducer 197 for enhancing penetration of ozone-containing gas, as described above.

Each chamber preferably also features a suction pump 198 provided with a catalytic filter. Suction pump 198 creates a negative pressure within the chamber during treatment, thereby reducing the risks of ozone leakage.

Figure 19:
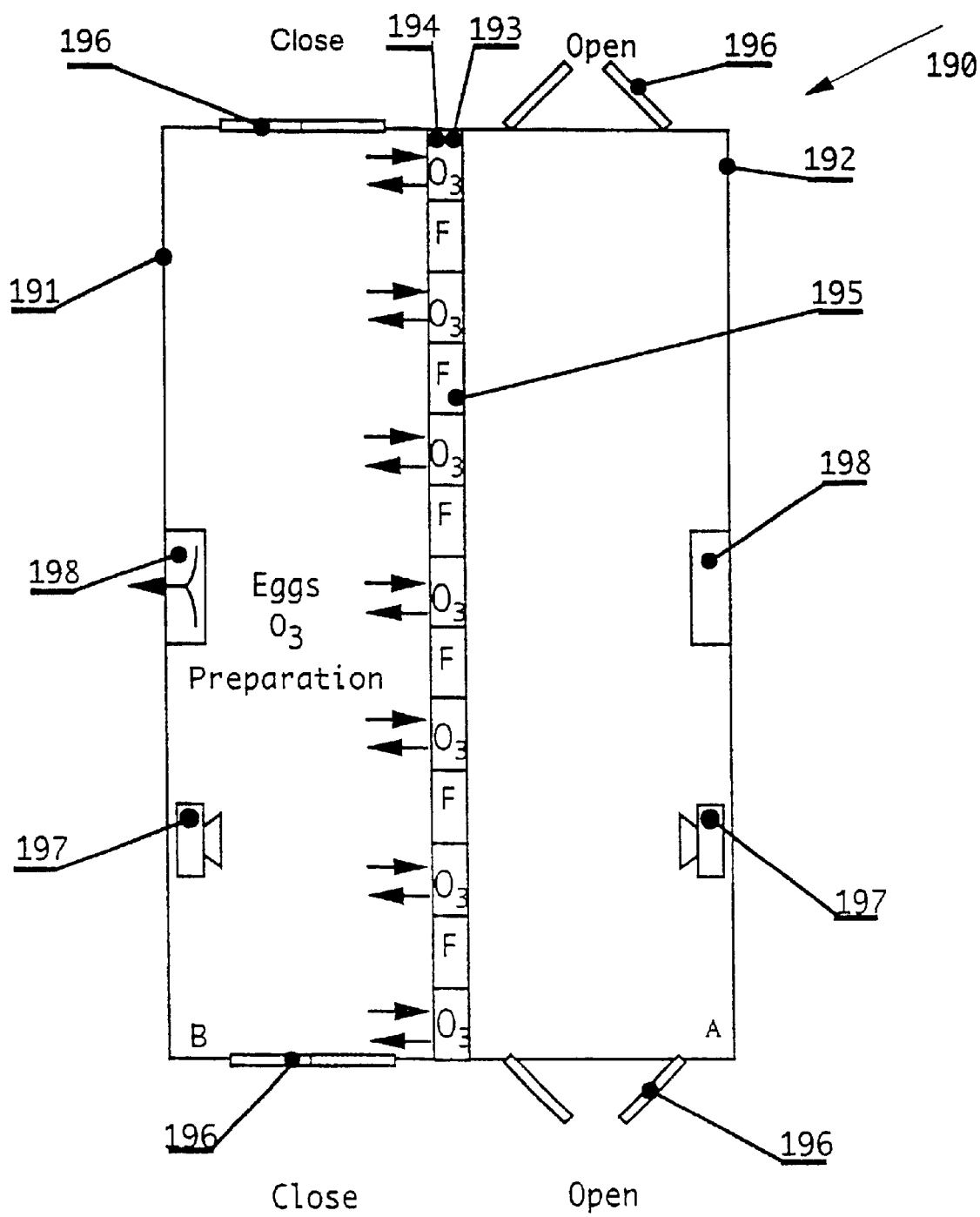
FIG. 19 is a schematic plan view of a two chamber system for batch treatment with an ozone-containing gas mixture, the system being shown at a first stage of operation.
Figure 21:
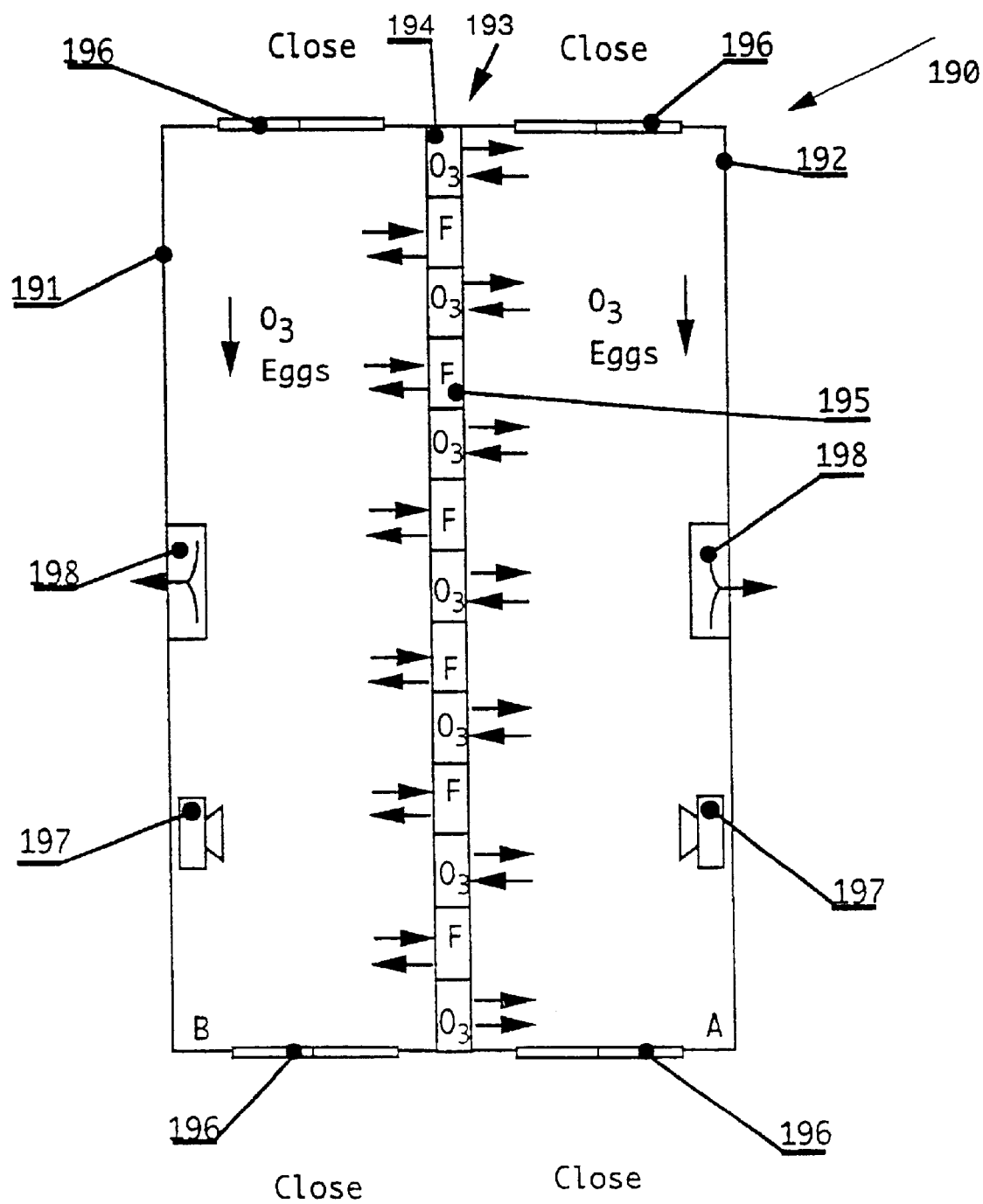
Figure 22:
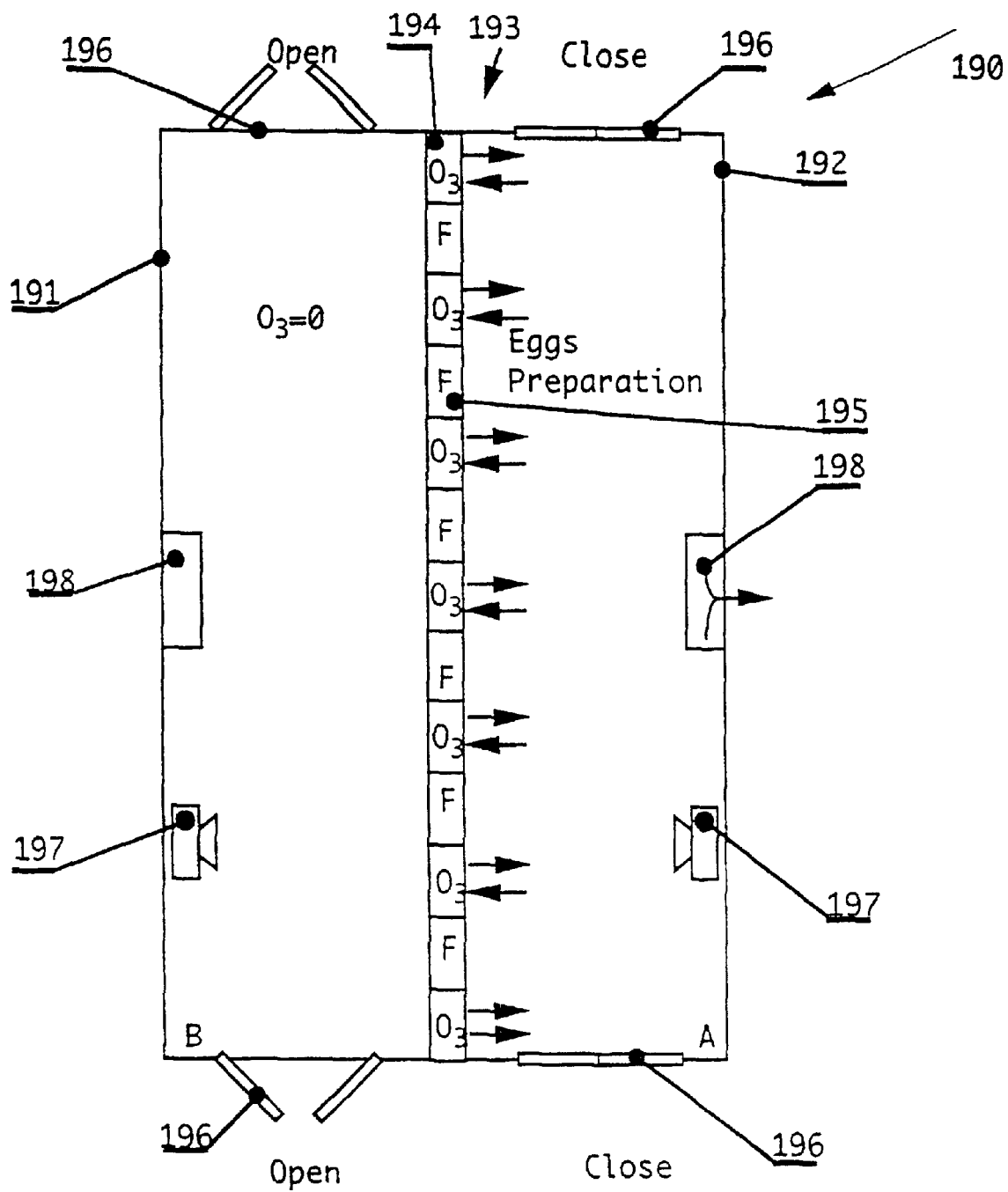
Figure 23:
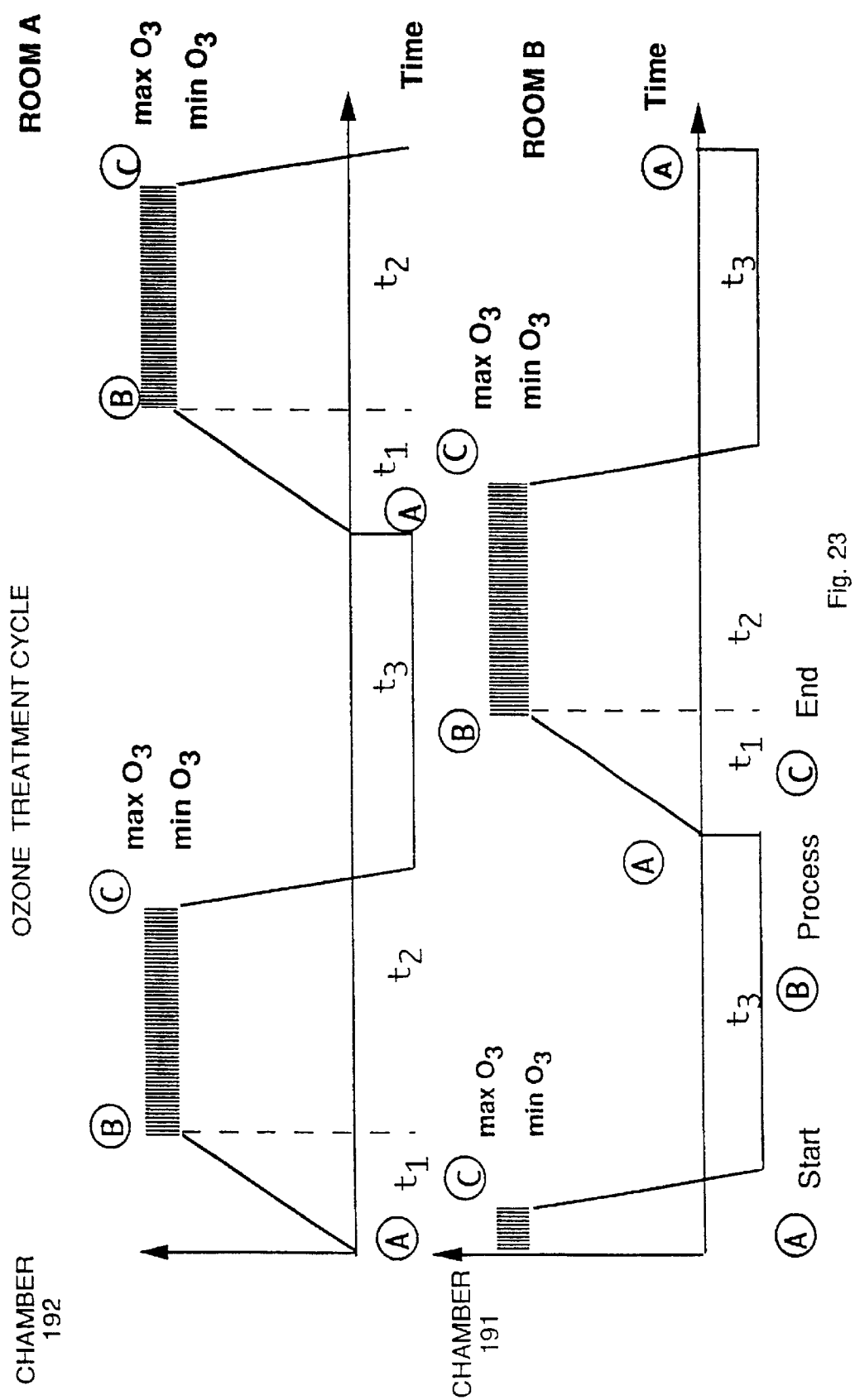
FIG. 23 is a schematic plot of the time variation of ozone concentration within each chamber of the system of FIG. 19.

FIGS. 19–22 show a sequence of steps in the operation of system 190, while FIG. 23 shows the corresponding time variation of ozone concentration within the two chambers. First, FIG. 19 shows system 190 at an arbitrarily chosen initial time with first chamber 191 performing ozone treatment while second chamber 192 is ozone-free for unloading and loading. At this stage, ozone generators 194 operate in recirculation mode within chamber 191, maintaining the ozone concentration at the maximum desired level. The suction pump 198 of chamber 191 also operates to maintain an inward pressure gradient, preventing the escape of ozone.

Figure 20:
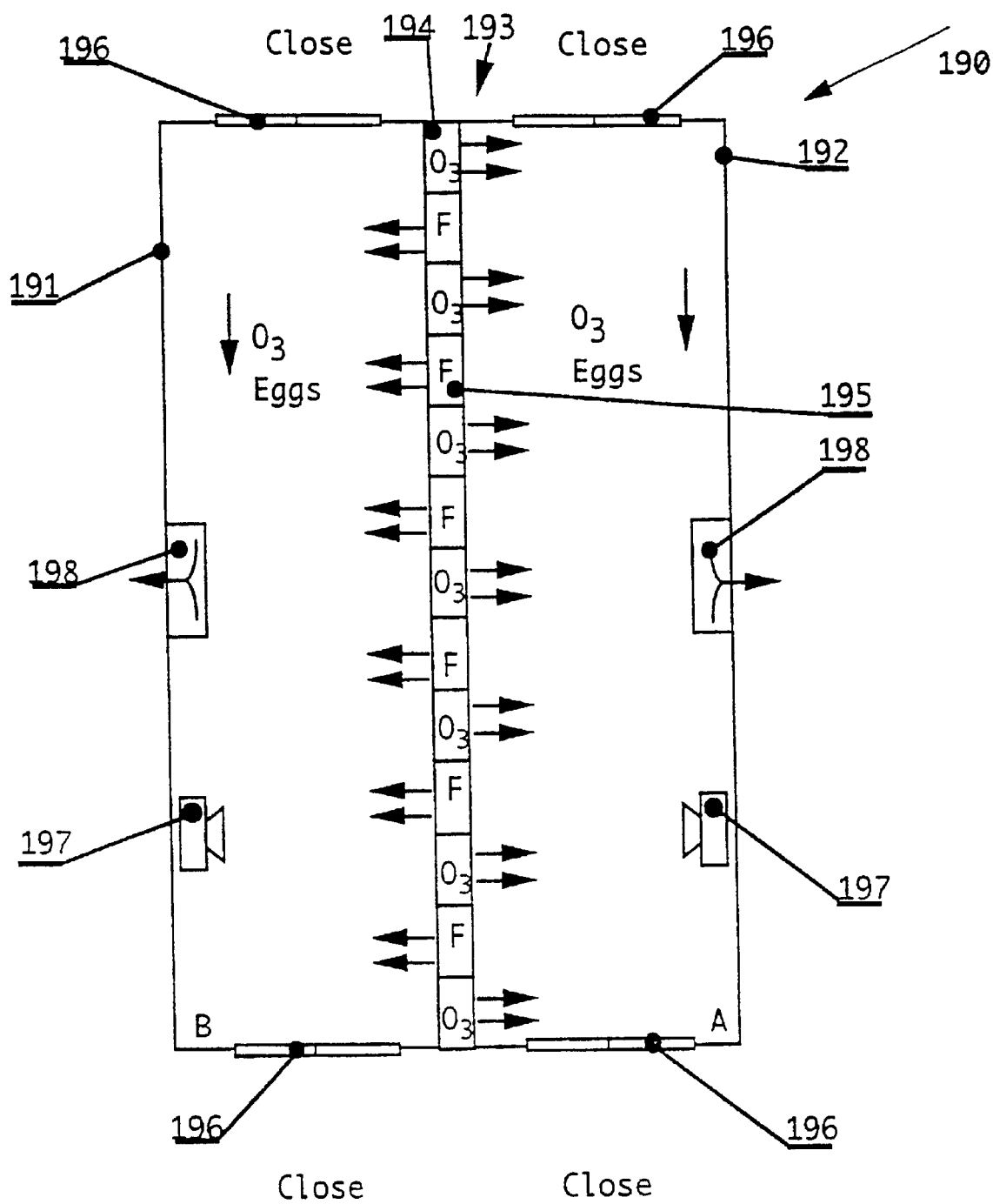
FIGS. 20, 21 and 22 are view similar to FIG. 19 showing three successive stages of operation of the system.

Once chamber 192 has been loaded and the treatment of chamber 191 is complete, all doors 196 are closed and system 190 enters a change-over stage shown in FIG. 20. Here, ozone generators 194 operate in a pumping mode transferring ozone-laden gas from chamber 191 to chamber 192. The reverse flow occurs through catalytic filters 195 which break down any ozone trying to return to chamber 191. As a result, the ozone concentration within chamber 192 rises rapidly while that of chamber 191 drops. At this stage, both suction pumps 198 operate to prevent leakage.

When the ozone concentration within chamber 192 exceeds that within chamber 191, the system enters a two-sided recirculation stage shown in FIG. 21. Here, ozone generators 194 operate in recirculation mode within chamber 192, raising the ozone concentration up to the maximum desired level for treatment. At the same time, catalytic filters 195 operate in recycle mode within chamber 191, removing any residual ozone.

Once the ozone content of chamber 191 is zero, filters 195 and suction pump 198 of chamber 191 are deactivated, as shown in FIG. 22. Once the pressure equalizes with atmospheric pressure, doors 196 are opened for unloading and re-loading of chamber 191. At the same time, treatment within chamber 192 continues as in the previous stage. The entire procedure is then performed in the opposite direction, i.e., with the roles of chambers 191 and 192 reversed, to treat the next batch.

Turning now to a more detailed consideration of ozone generator structures according to the present invention, these will be described in detail with reference to FIGS. 24–45.

By way of summary, the ozone generators or "ozonators" of the present invention are versatile systems for producing ozone from an oxygen-containing gas which provides a homogeneous mixture of ozone and the said gas (referred to as "carrier gas"). The ozonators include at least one frame the area of which is covered by at least two electrodes, coated with a dielectric material, which are distributed in parallel, whereby between them exist gaps for gas flow at an angle of substantially 90° to the longitudinal axis of the electrodes and the frontal plane of the frame area, the surface areas of the electrodes being substantially parallel with the surface area of the electricity-conducting material from which the electrodes are made, the electrodes of the same polarity being connected together, the electrodes of opposing polarities being adjacent to each other and the electrodes being placed in a position substantially perpendicular to the gas stream entering the system. The system for producing ozone is versatile. having the advantage of facilitating on-site ozone production with a wide range of desired concentrations, thus enabling various applications that were before difficult, non-feasible or even impossible.

The system also has a compact construction and occupies a relatively small space.

An important parameter in the production of ozone in the ozonator according to the present invention, is the ration of electrode surface area to the cross section area of the gas flow duct tube. This ration is above 0.4, when the length of the electrode is 10 times greater than its diameter. As oxygen molecules ($O_2$) pass through the electric current generated between the electrodes, some molecules are dissociated and form monatomic Oxygen (O), and then a part thereof being recombined forming ozone ($O_3$). The electrodes cross-section shapes may vary and are kept geometrically compatible with each other.

Control of being turned around their longitudinal axis, thus narrowing or widening the gaps between the electrodes where the reacted gas flows, in order to facilitate regulation of the gas flow rate.

The electrodes can be made of any electrically conducting material. Such as metallic wire, film of power, carbon wire or film and electricity conducting liquids and gels. The electrodes' dielectric coating may be selected from various materials such as borosilicate glass or ceramic, having a high dielectric constant, typical values being in the range of between 4 to 7 and a high breakdown voltage, preferably above 12 KV/mm.

The electrodes' cross section shape may vary, provided an equal gap (distance) is maintained between them, in order to provide a uniform electric field between the electrodes.

The gaps between the electrodes of said apparatus are at an angle of substantially 90° to the longitudinal axis of the electrodes and the electrodes are kept substantially parallel to each other, in order to obtain a uniform electric field throughout the entire space where the ozone is formed.

The frame holding the electrodes can be made of different kinds of insulating materials, which are not attacked by ozone thus enabling the choice of certain types of materials suitable for a certain use. Generally, it is possible to use any ozone-resistant material. It should be emphasized that this issue is not so critical and generally any material can be used, provided it is suitable for its specific purposes possessing a sufficient durability, flexibility, elasticity and the like.

The control of ozone concentration level is achieved by monitoring the flow rate of the gas through said ozonator and/or by changes in the electric field between the electrodes, which is done by controlling the voltage applied across the electric terminals of said ozonator.

A particular advantage of the ozonator system according to the present invention is its applicability where there is no room for an additional mixer, such as in the case of narrow gaps for air.

Figure 24:
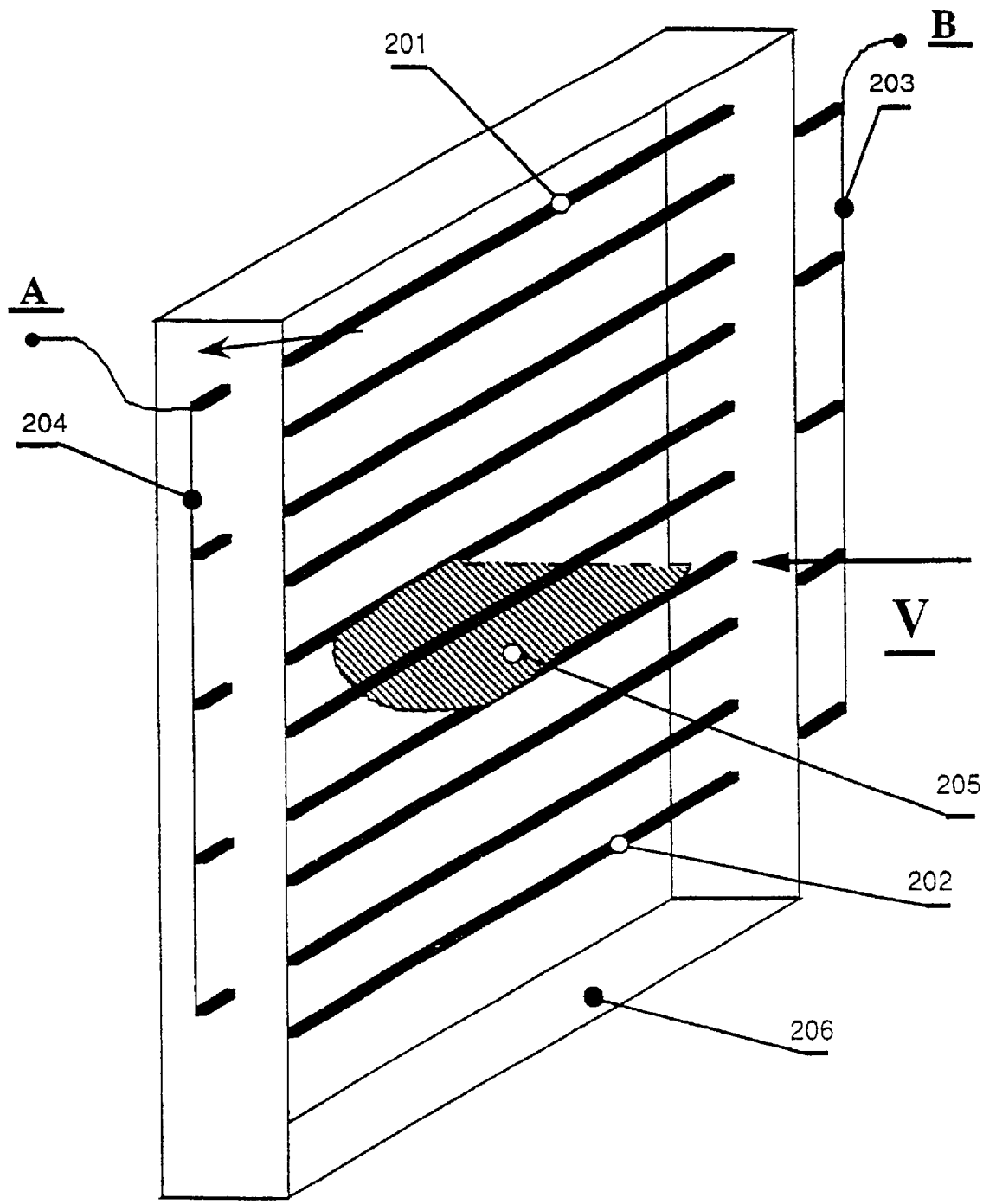
FIG. 24 illustrates an embodiment of a frame of the Multipurpose Versatile Ozonator.

Turning now to the features of frame ozonators in more detail, FIG. 24 illustrates schematically a possible embodiment of a frame of the ozonator according to the present invention. The frame consists of electrodes (201,202) coated with a dielectric material in an array, substantially parallel to each other. Between the said electrodes exist gaps at an angle substantiality 90° to the longitudinal axis of the electrodes and the frontal plane of the frame area. The surface area of the electrodes is substantially parallel to the surface area of the metal conductor from which the electrodes are made. The electrodes of the same polarity are electrically connected together (203,204) and arranged so that the electrodes of opposite polarities are adjacent to each other. The said setup is held together by a confining rectangular frame (206). A high voltage (AC) is applied to said electrodes, connected across terminals A and B. A flow of air or a gas containing oxygen is passed through the frame, applied perpendicularly to the frontal surface area of the frame, in order to achieve a maximum efficiently of ozone production. As the oxygen molecules ($O_2$) pass through the electric field generated between the electrodes, some molecules are dissociated and form monatomic oxygen (O) and then recombine, in part, to form ozone ($O_3$).

Figure 25A:
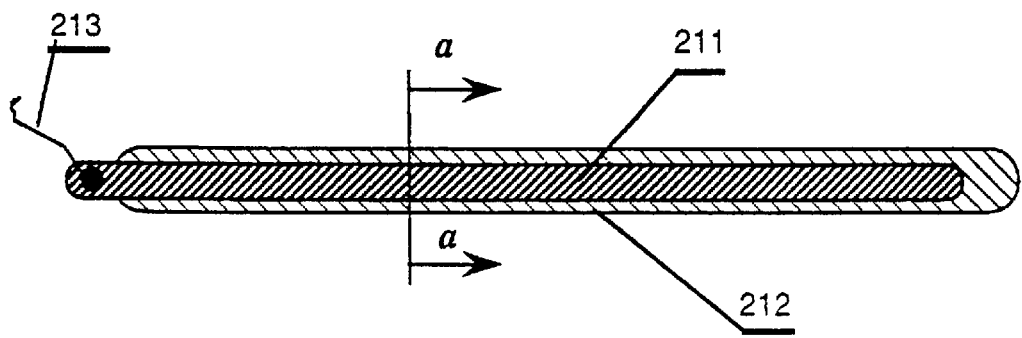
FIGS. 25a and 25b illustrate an assembly of an electrode used in said ozonator.
Figure 25B:
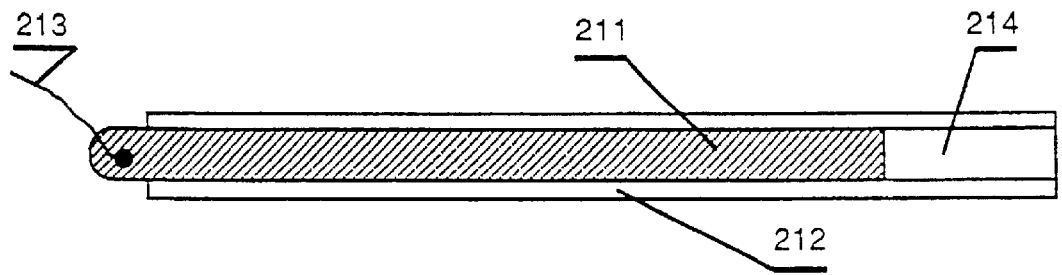

FIG. 25 illustrates schematically an assembly of an electrode used in the ozonator according to the present invention. The assembly comprises a metallic electrode (211), a dielectric coating (212), an electric contact (213) and an insulating space (214). The electrodes of said ozonator can be of various designs, two typical ones being illustrated in FIG. 25. As shown, an electrode is coated with a dielectric material on all sides except for the electric contacts (202a), or an electrode is placed inside insulating tubing, where at the end there is an insulating hollow space preventing an electric discharge between the electrodes.

FIG. 26 illustrates some typical cross section shapes of electrodes most suitable for the ozonator according to the present invention.

FIG. 26a depicts electrodes having a polygonal cross section shape. having a metallic electrode (221),a dielectric coating (222),wherein the direction of gas flow is indicated by V and the space for ozone formation is indicated by G.

FIG. 26b depicts electrodes having a circular cross-section.

FIGS. 26c and 26d illustrate cross-sections the electrodes having different shapes but compatible with each other in terms of the corresponding shapes of the space between them. They comprise a metallic electrode (221) and a dielectric coating (224), the ozone being formed in the space (G).

FIG. 26e depicts electrodes with a cross section which enables a space with parallel-border surfaces, thus facilitating the control of gas flow through the electrodes, by rotating the electrodes around their longitudinal axis.

FIG. 27 illustrates a particular use for said ozonator in an air vent or a chimney.

Figure 27A:
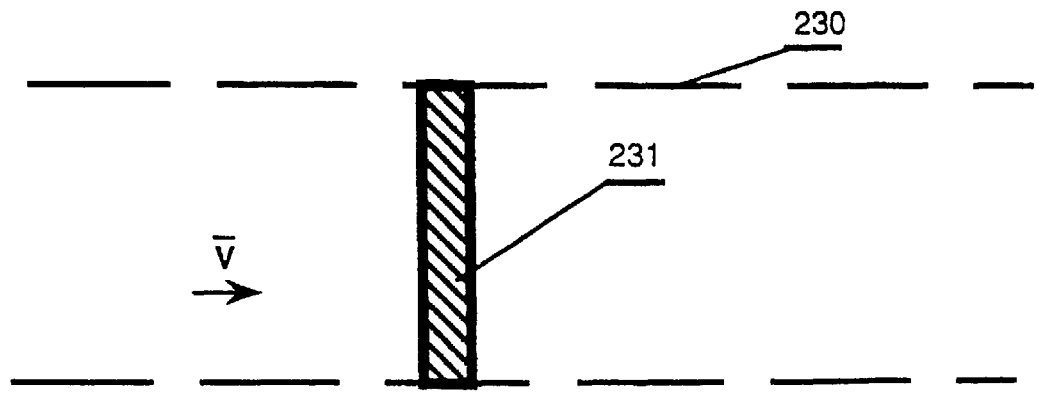
FIGS. 27a and 27b illustrate a typical use for said ozonator in an air vent or a chimney.

FIG. 27a shows the use of an ozonator according to the present invention installed inside an air vent or a chimney. It comprises an air vent (230), an ozonator according to the present invention (231), the direction of gas flow being indicated by V. This system is intended for purification and sterilization of the treated medium.

Figure 27B:
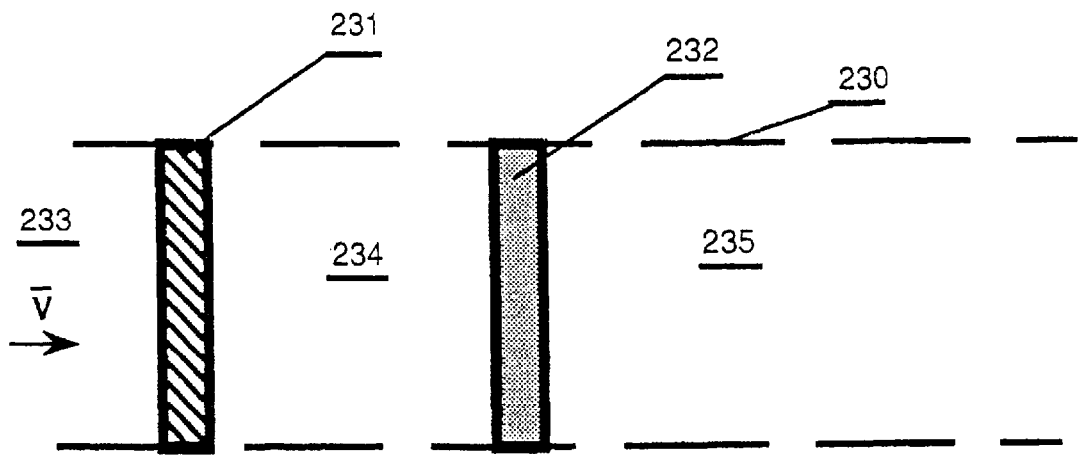

FIG. 27b illustrates a similar compilation installed inside an air vent, with a device for eliminating the ozone residues after completion of an air treatment in said system. As can be noticed, there is a catalytic filter (232) mounted inside said system, having an external space (233) of the vent in front of the ozone treatment area, the space where the ozone treatment is applied (234), and the space where ozone residues are removed by a catalytic filter (235) after the treatment. This system is intended for purification, sterilization as well as deodorization of air or other gases. Such a system can be used in air conditioning setups and refrigerators of various sizes.

The ozonator system according to the present invention is also suitable for treating air or oxygen contaminated with microorganisms or chemical contaminants. The ozone after said treatment will be transformed into oxygen molecules along with a decontaminated gas, and ozone-free.

Figure 28:
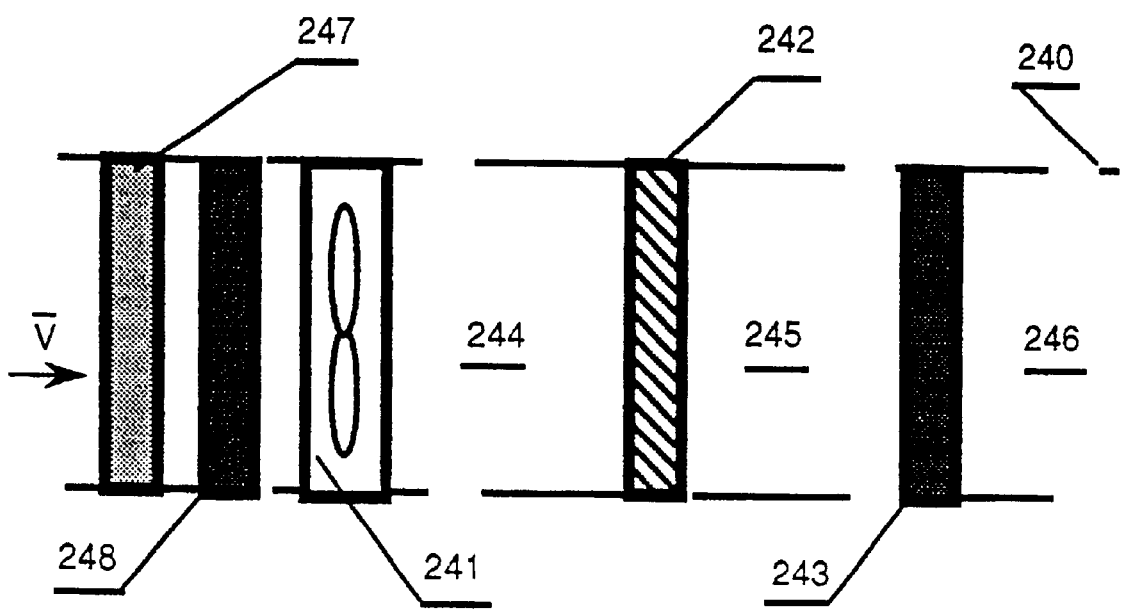
FIG. 28 illustrates a system for purification and disaffection of air, using said ozonator and a blower.

FIG. 28 illustrates a system for purification and disinfection of air, using the ozonator according to the present invention and a blower. The system comprises:

- a cabinet (240);
- an integrated blower (241);
- an ozonator according to the present invention (242):
- a catalytic filter (243);
- an external space on front of the ozone treatment area (244);
- a space where the ozone treatment is applied (245);
- an internal space after the catalytic filter (246);
- a filter for the removal of dust particles (247), placed before the blower;
- a second catalytic filter (248), to prevent the release of ozone caused by a reverse flow of gas (optional).

Figure 29A:
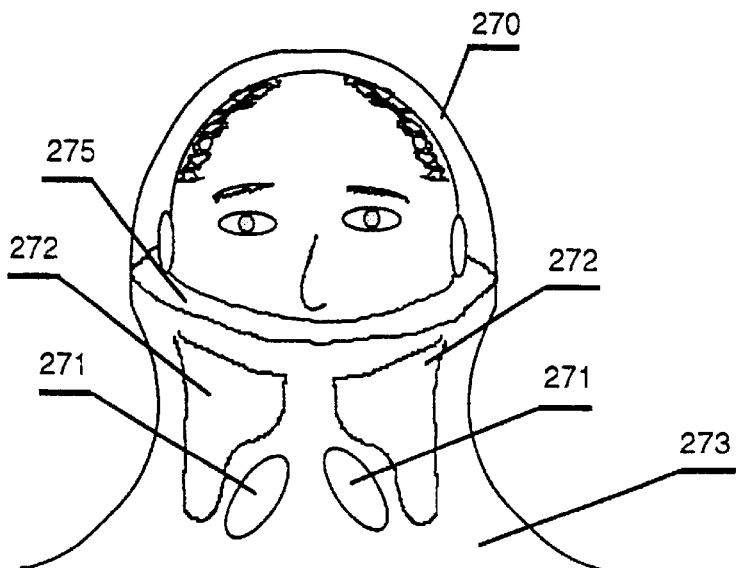
FIGS. 29a–29c illustrate a typical use of said ozonator in a personal and/or external protection hood.
Figure 29B:
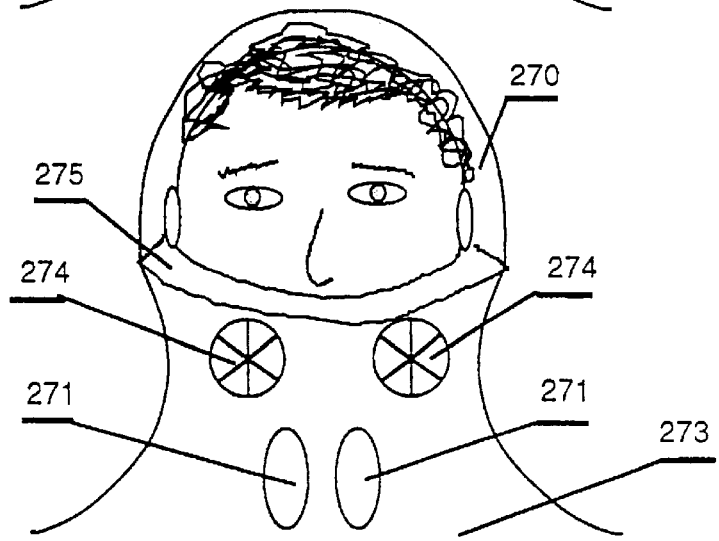
Figure 29C:
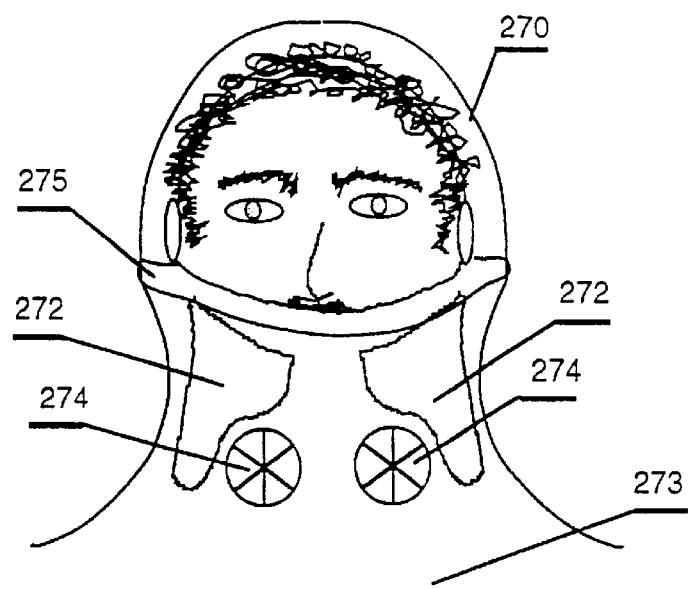

FIG. 29 illustrates a typical use of the ozonator in a personal and/or external protection against microbiological contaminants.

The inhaled air as well as the exhaled air are disinfected by ozone, prior to passing through the catalytic filters, thus ensuring protection for a person wearing the hood from infection through the ambient air wearing the hood. In a case that infection already exists, it ensures protection from infection for other persons.

FIG. 29b depicts a hood for personal protection where only the inhaled air is sterilized. This hood may be used by people who come in contact with patients confined to a sterile room, such as patients suffering from deficiencies of the immunological system, in order to avoid infection of such people.

The hood comprises the following items:

- a transmit shield (270);
- an ozonator as describes above, including a catalytic filter on each side of the ozonator, for sterilizing inhaled air (271);
- a catalytic filter on each side of the ozonator for sterilizing the exhaled air (272);
- a sheet to be secured to person's chest (273) in order to avoid penetration or leakage of air to and from said hood not through said ozonator, and
- check valves (274) which regulate the inlet and outlet of air.

In order to avoid moisture condensation, a membrane may also be installed to separate the compartment for the exhaled air from the rest of the hood (275).

Figure 30:
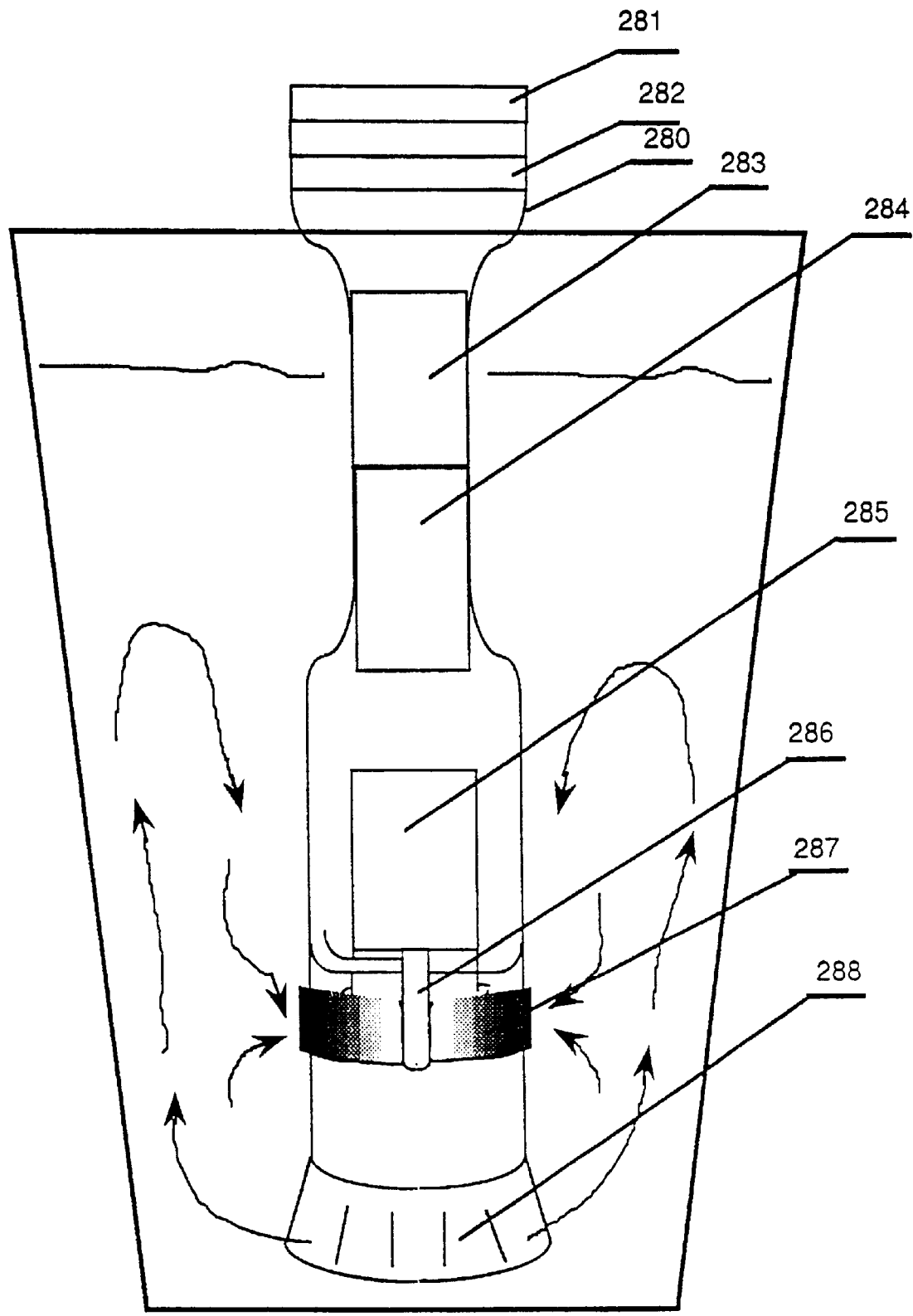
FIG. 30 illustrates a preferred personal setup for water treatment using said ozonator.

FIG. 30 illustrates a preferred personal setup for water treatment, using an ozonator according to the present invention, especially designed to be immersed in a container for drinking water.

The setup comprises the following items:

- a cylindrical housing (280);
- a particle removing filter (281) incorporating also a catalytic filter;
- an ozonator according to the present invention (282);
- a battery cartridge (283)
- an inverter for high voltage (284)—when necessary-;
- a water pump (285);
- a Venturi device (286);
- a catalytic filter (287), and
- an outlet for the purified water (288).

The operation for water treatment is as follows. The water is pumped through a Venturi device which sucks in air through the filter (281) and the ozonator (282). During the passage of water through the Venturi device, it mixes homogeneously with the ozone-containing air. The mixture flows through the outlet (288) into the purified water container. After the purification is complete, the ozonator operation is stopped but the pump remains in operation for an additional period of time, in order to enable a complete elimination of any ozone residues, by passing the gas through the catalytic filter.

Figure 31:
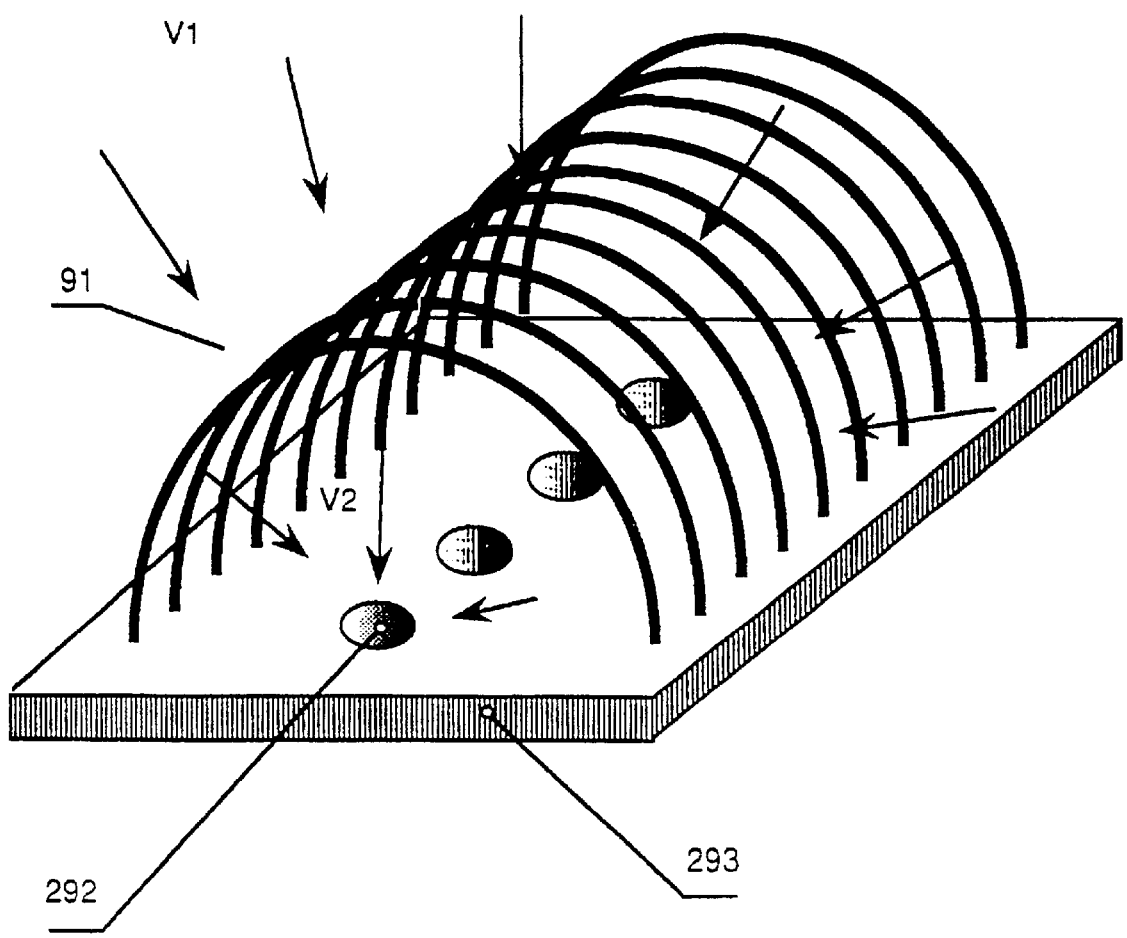
FIG. 31 illustrates an embodiment of the ozonator system which comprises an arc-shaped frame.
Figure 32:
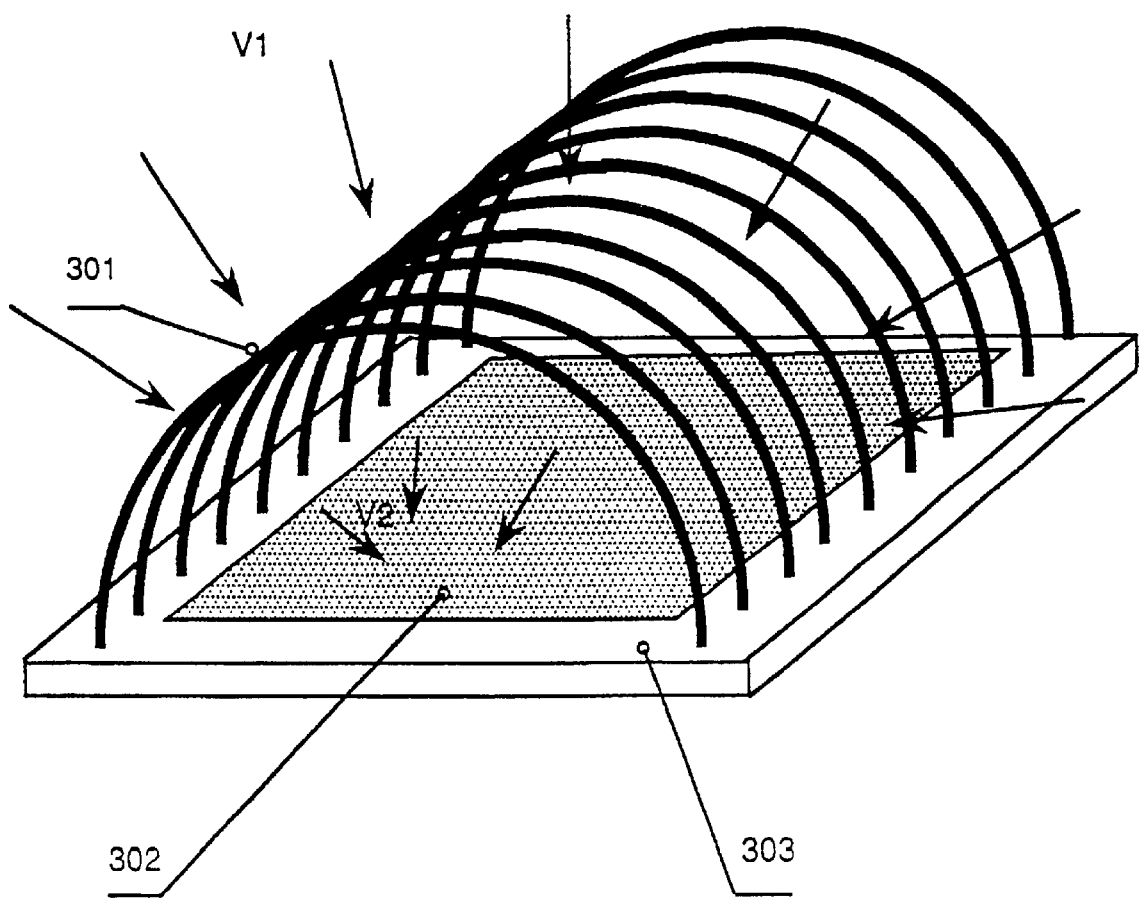
FIG. 32 illustrates a variant of the embodiment given in FIG. 31. wherein said system consists of a tunnel constructed from arc-shaped frames.
Figure 33A:
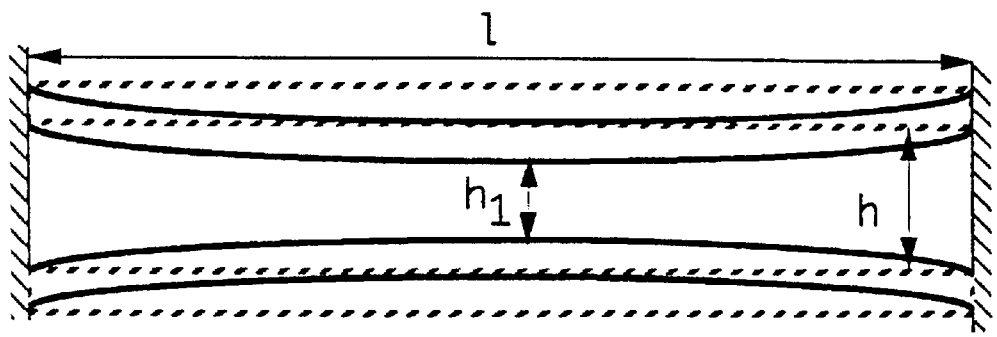
FIGS. 33a and 33b are a schematic representation of the movement of adjacent electrodes of an ozone generator during operation.
Figure 33B:
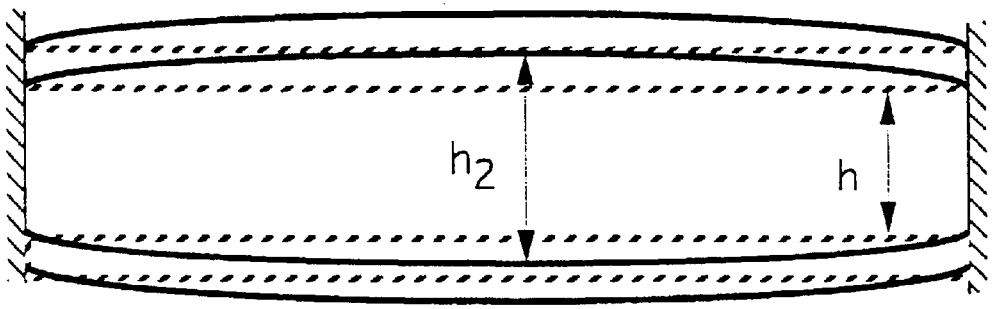

FIGS. 31 and 32 illustrate another embodiment in which the electrodes are characterized by their arc-like shape which facilitates locating them around a conveyor, on which solid objects can be continuously treated by the homogeneously distributed ozone.

According to another mode of use, the container in which the ozone is dispersed can be fitted with shelves on which solid materials to be treated by ozone, such as a fresh agricultural produce, food products, packaging materials or equipment that has to be sterilized, can be loaded. Thus, for example, in case of fruits and vegetables, disinfection can be carried out without affecting the natural waxy coating on the fruit surface, using ozone concentration ranging up to 10 ppm. at a relative humidity ranging up to 98% and a temperature ranging between 0 to 40° C., the disinfection operation took about 5 to 100 minutes.

At the outlet of the container, the ozone is conversed back into oxygen. In cases where even traces of ozone are undesirable, it is possible to provide at said outlet a trap containing a solution of a reducing agent or a catalytic filter such as carbon, which will readily eliminate said residues.

FIG. 31 is a schematic illustration of a tunnel constructed from arc shaped electrodes, to be used along and around a conveyor, on which the solid materials or objects, such as agricultural produce, could be treated by ozone in a continuous manner. The following items can be noticed:

291: The arc-shaped electrodes;
292: the air-suction opening;
293: base of the tunnel;
$V_1$: base of the tunnel, and
$V_2$: ozone containing air.

FIG. 32 is similar to FIG. 31, with the following items:

301: Arc-shaped electrodes;
302: porous base for air suction;
303: base of tunnel:
$V_1$: air inlet, and
$V_2$: ozone-containing air.

Above the surface of the tunnel, there is a conveyor having a porous film, the solid material to be treated with ozone being moved along the conveyor belt. The ozone gas after its contact with the solid material, is driven out from the tunnel through the outlet $V_2$. Optionally, a mobile device may be located in said tunnel, on which the material to be treated could be suspended.

According to another preferred embodiment, a device is located in said tunnel for turning said material alternatively from one side to the other, at least once during the ozone treatment, in order to assure its contact with ozone on the entire surface.

In regard to all of the aforementioned ozonator structures, as well as those to be described below, it is a preferred feature of the present invention that the electrodes are formed using polyvinyl-difluoride (PVDF) as the dielectric insulator.

It has been found that conventional glass coated electrodes suffer from various physical effects which reduce both efficiency and reliability. These effects are thought to be a result of the gap which exists between the conductive core and the glass layer, allowing destructive penetration of oxygen.

Use of PVDF allows production of electrodes by injection molding techniques, ensuring intimate contact between the dielectric material and the conductive core. Injection molding techniques also allow one-step production of entire self-contained ozonator units, as will be described below. Suitable injection molding techniques are well known in other electrical component applications in which injection molding of other plastic materials is performed with implanted conductive material.

PVDF provides a number of other advantageous features. Besides the required properties of having a high dielectric constant and being inert under the operating conditions of the ozonator, PVDF also exhibits significant elasticity. As a result, structures formed from PVDF are considerably fracture resistant, and therefore more reliable and durable than equivalent structures made with glass. The flexibility can also be used structurally such as in clip-on connectors, as will be described below.

Turning now to FIGS. 33–43, various refinements of the ozonator structures of the present invention will now be described. First, by way of introduction. FIGS. 33a and 33b illustrate the effects of resonant motion of elongated electrodes 310 of length l. During operation of the ozonator, large magnetic fields are caused in the vicinity of the electrodes, resulting in various forces between them. Where more than two electrodes are involved. complicated vibrations in more than one plane may result. As a result of these vibrations, the gap between adjacent electrodes. initially h, varies along the length of the electrodes between a minimum value $h_1$ (FIG. 33a) and a maximum value $h_2$ (FIG. 33b). This vibration has a number of undesirable effects: firstly, ozone generation is reduced during the proportion of time that the gap width is increased; secondly, the reduced gap spacing is accompanied by a risk of sparking across the gap; and thirdly extreme mechanical vibration may result in breaking of the insulating dielectric coating of the electrodes, or even snapping or destructive collision of adjacent electrodes.

For the above reasons, it has been found that there is an effective "critical length" beyond which the electrodes become mechanically unstable. By way of example, in the case of electrodes with an aluminum core of 1.6 mm diameter and a PVDF dielectric insulator of thickness 1.2 mm (total diameter 4 mm), the critical length has been found to be about 30 cm. For increased stability and reliability. a length of about 20 cm is preferred. In more general terms, the critical ratio (the ratio between critical length and electrode diameter) is close to 80 for an aluminum/PVDF electrode, and about 100 for a pyrex-coated electrode.

The limitation of electrode length to less than a given critical value leads to a problem in construction of large area ozonators. A rudimentary solution to this problem is addition of intermediate electrode spacers at intervals less than the critical length. However, this solution is highly labor intensive, requiring precise manual positioning of spacers between the electrodes during assembly, or use of a mold which would need to be unrealistically large.

A preferred solution is provided according to the teachings of the present invention by a modular frame-ozonator assembly, generally designated 312, which will be described with reference to FIGS. 34–42.

Figure 34:
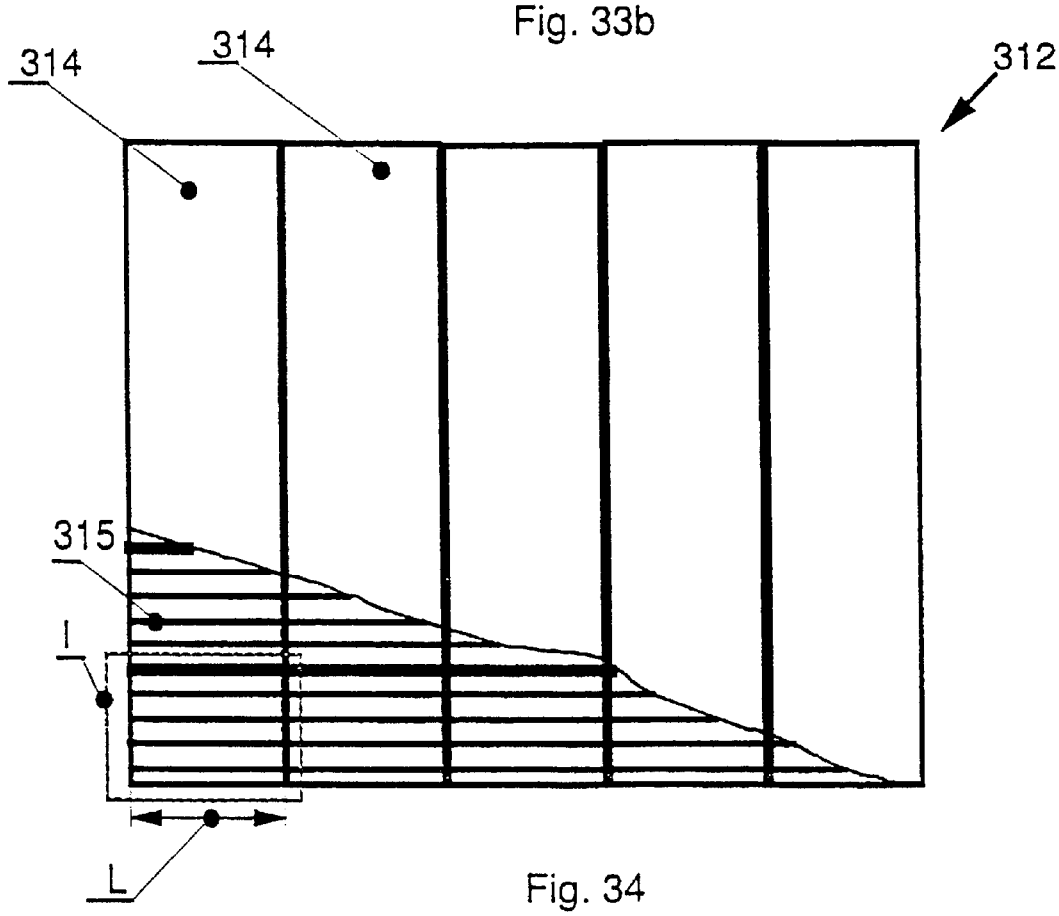
FIG. 34 is a schematic front view of a modular ozone generator assembly, constructed and operative according to the teachings of the present invention.
Figure 35:
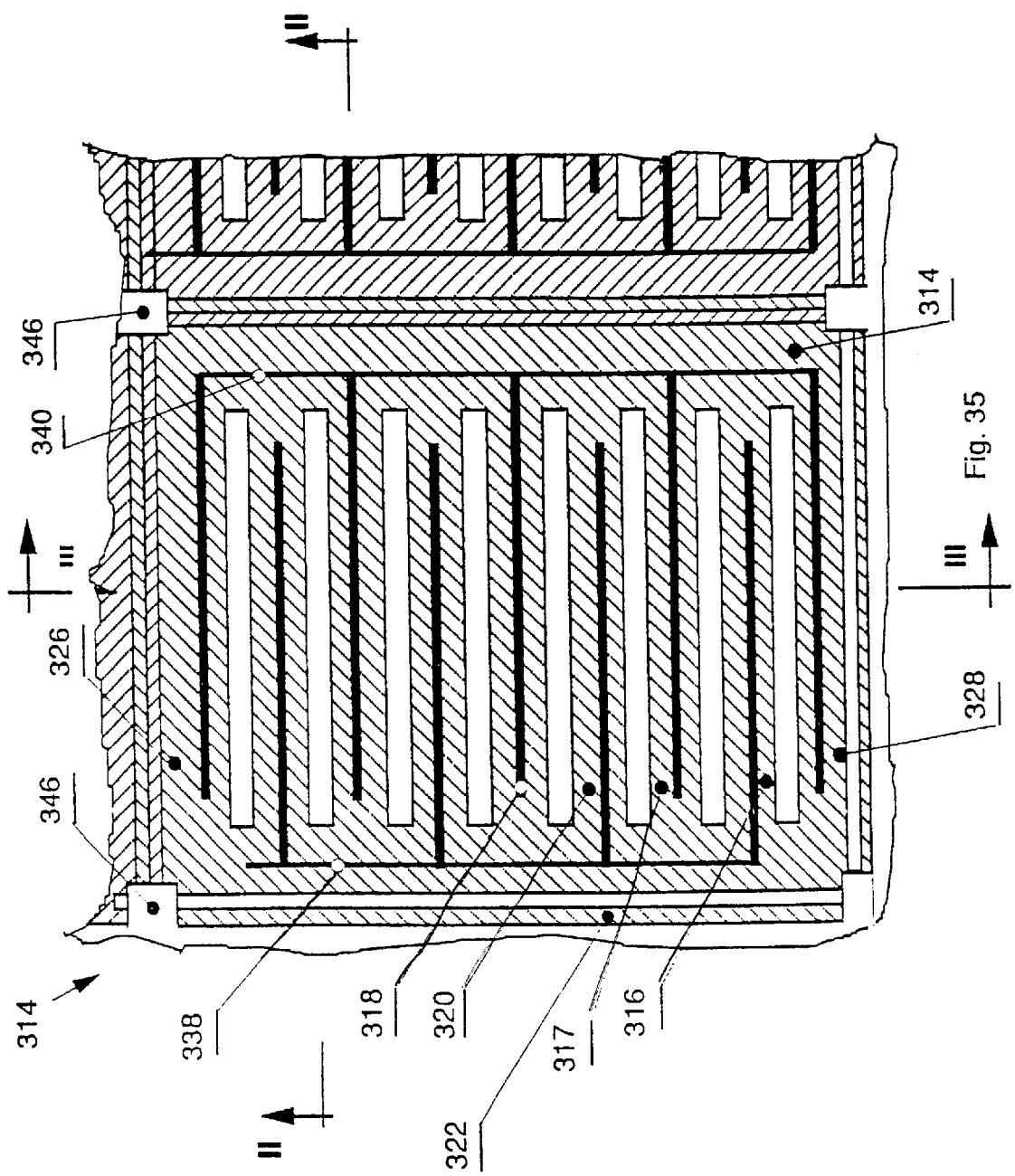
FIG. 35 is a simplified cross-sectional view through a module corresponding to region I of FIG. 34.
Figure 36:
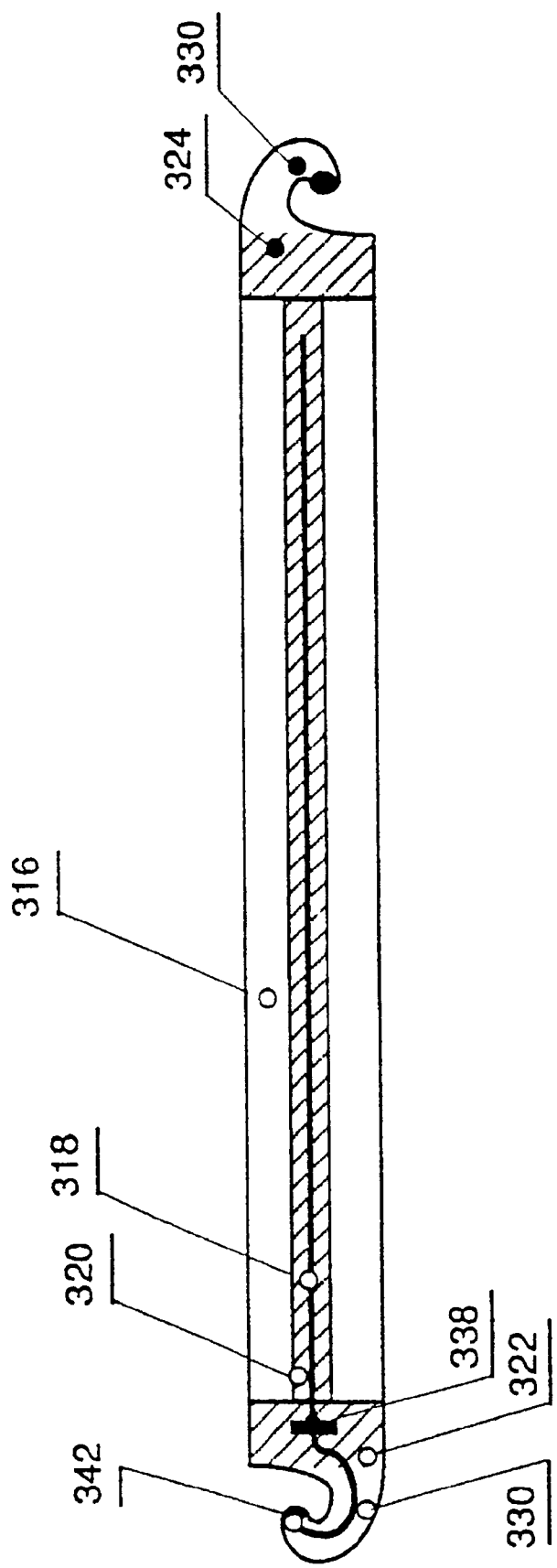
FIG. 36 is a cross-sectional view taken along the line II—II of FIG. 35.

FIG. 34 shows assembly 312 made up of an array of identical modules 314. Each module 314, shown in detailed section in FIG. 35, has a number of elongated electrodes 316, 317 of length l less than the critical length arranged to form a self-contained frame ozonator unit. This modular structure allows convenient construction of an ozonator of any desired area and size while avoiding the problems usually encountered with large area ozonators.

Turning now to the details of module 314, each electrode 316, 317 is formed from an electrically conductive core 318 covered by polyvinyl-difluoride 320. Electrodes 316, 317 are deployed in substantially parallel, equally spaced relation to each other so as to form a substantially flat electrode array with air gaps between adjacent electrodes. Electrodes 316 of a first polarity are interspaced between electrodes 317 which have opposite polarity.

Electrodes 316, 317 are supported by a substantially rectangular frame made up of first and second sides 322, 324 substantially perpendicular to the electrodes, and first and second ends 326, 328 substantially parallel to the electrodes. Preferably, there is no air gap between ends 326 and 328 and the adjacent electrodes since a gap in these positions would not contribute to ozone production.

First and second sides 322, 324 are formed with complementary interlocking forms so that first side 322 can be engaged with the juxtaposed second side 324 of a similar module 314 during construction of assembly 312. A preferred configuration of the complementary interlocking forms is shown most clearly in FIG. 36. Here, each side features a clip shape 330 such that adjacent modules can be semi-permanently forced into engagement.

Figure 37:
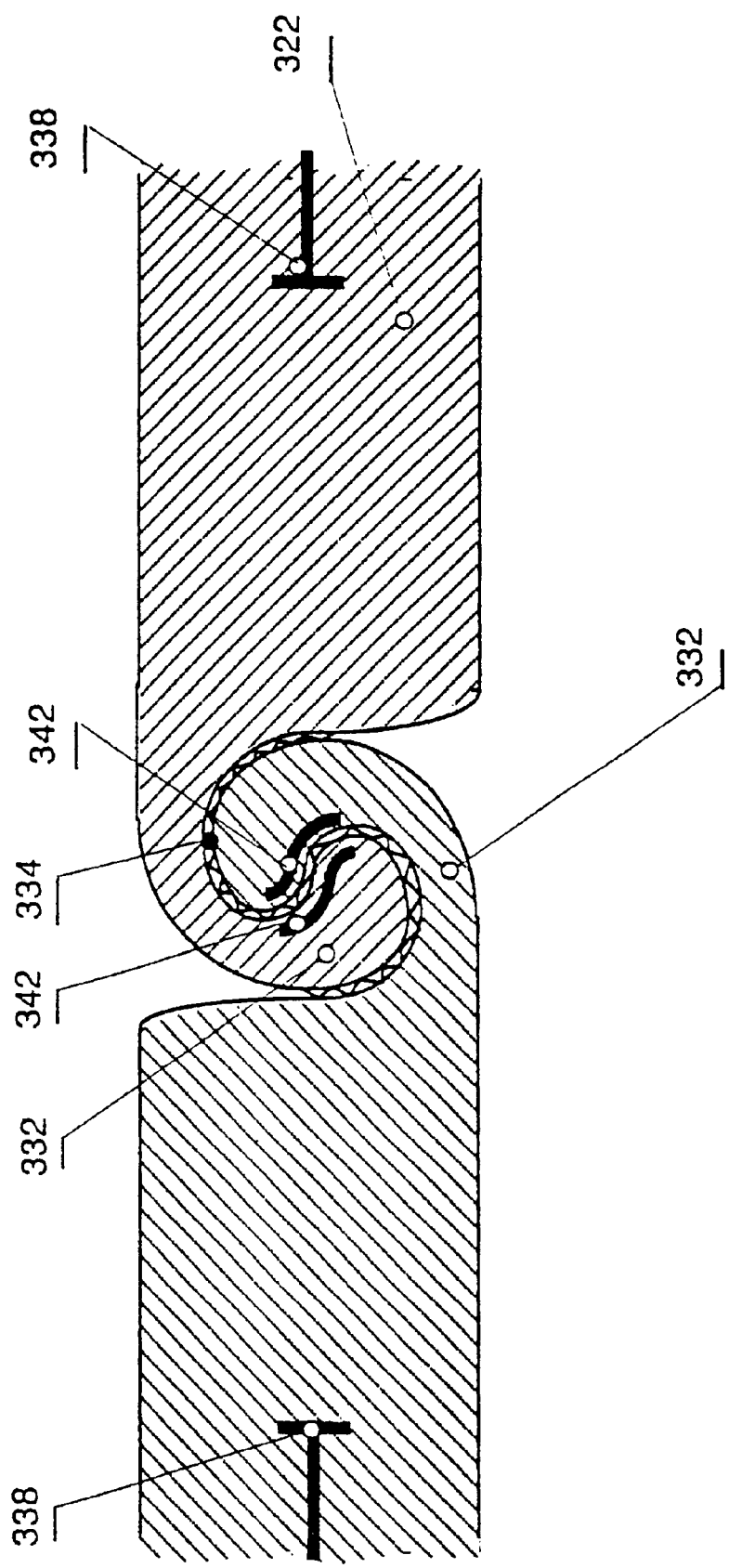
FIGS. 37 and 38 are detailed cross-sectional views showing variant interlocking shaped edges for use with the modules of FIG. 35.
Figure 38:
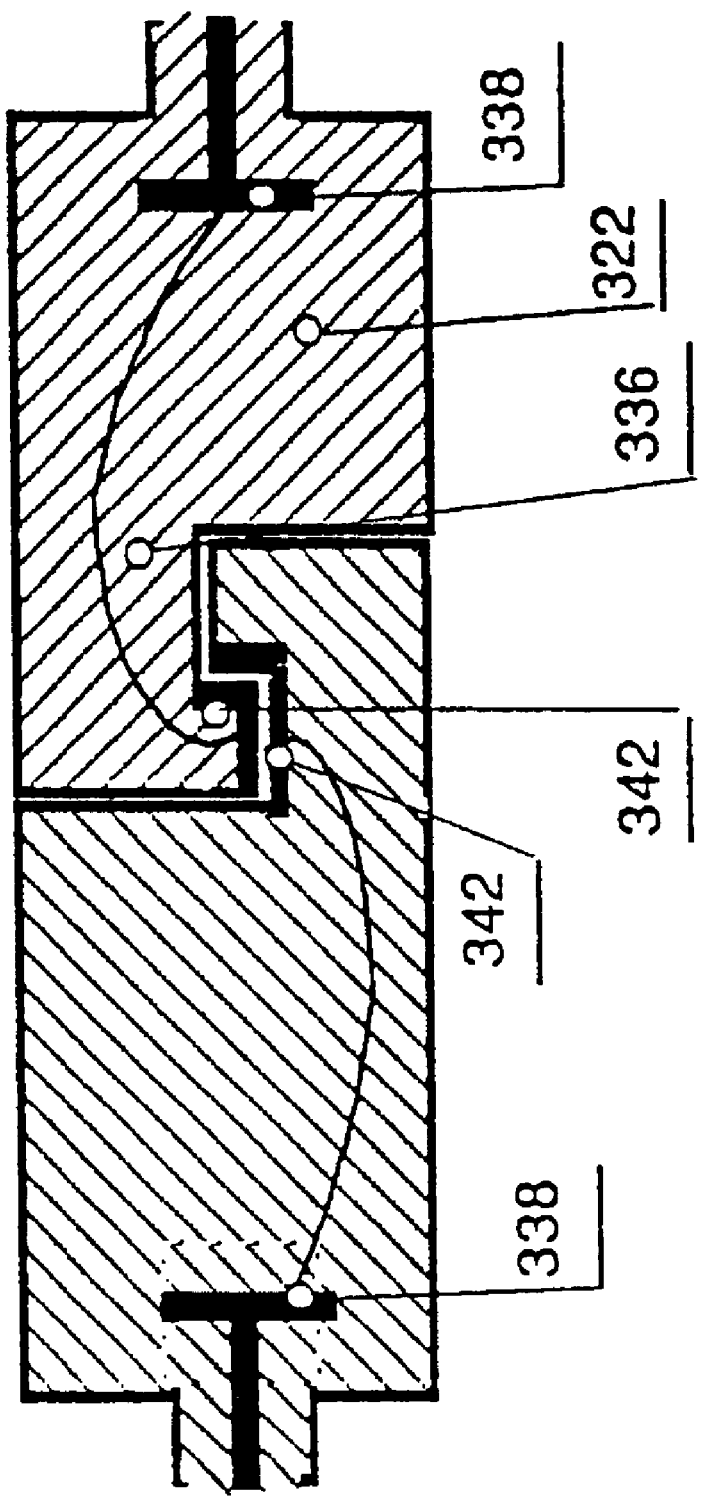
Figure 39:
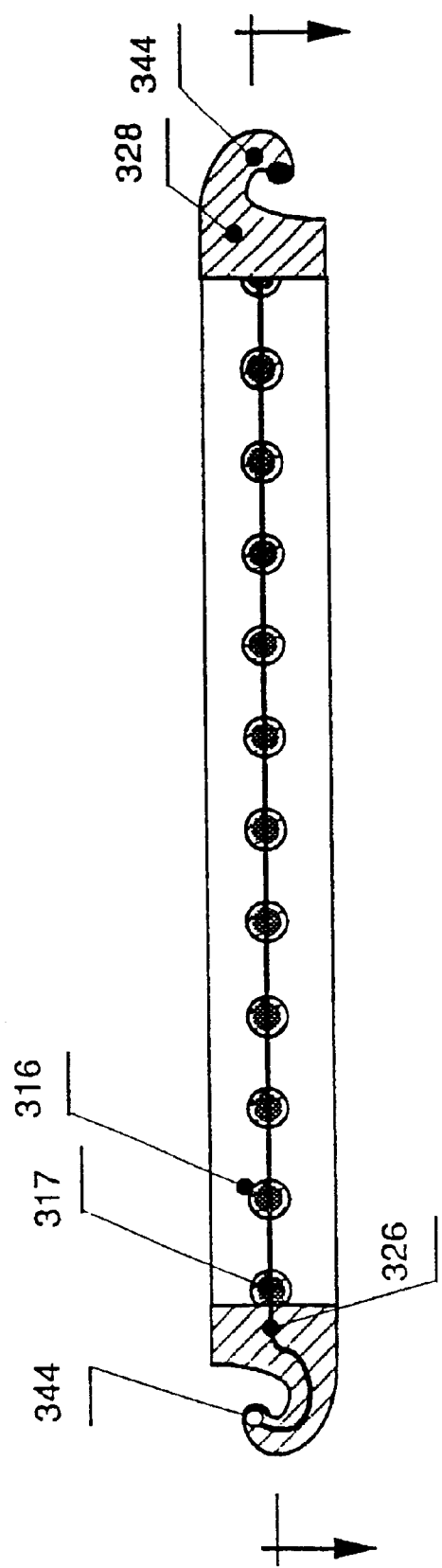
FIG. 39 is a cross-sectional view taken along the line III—III of FIG. 35.

Alternative preferred configurations of the interlocking forms are shown in FIGS. 37 and 38. FIG. 37 shows a clip shape 332. similar to clip shape 330, but with the addition of ratchet teeth 334 which lock the clips positively together in their engaged position. Disassembly of the connection, if required, can only be performed by sliding the modules apart along the length of sides 322 and 324. FIG. 38 shows a rectangular interlocking form 336.

Preferably, first and second ends 326, 328 are also formed with complementary interlocking forms so that first end 326 can be engaged with the juxtaposed second end 328 of a similar module 314 during assembly. An example of suitable interlocking forms can be seen in FIG. 39. The interlocking forms can take a range of shapes including, but not limited to, those described above with reference to sides 322, 324.

Turning now to the electrical connection of modules 314, all electrodes 316 of a first polarity are connected to a first common electrical connection or rail 338 and all electrodes 317 of opposite polarity are connected to a second common electrical connection or rail 340.

External connections to rails 338 and 340 may be achieved in many ways. Preferably, connectors 342, 344 (FIGS. 36–40) are built-in to the sides and ends of modules 314 in a manner to allow contacts to be made across assembly 312 without additional external wiring. In this case, the elasticity of the clip-together assembly maintains firm contact of the connectors once assembled, thereby preventing sparking across the connections.

Additional switchable multiconnector sockets 346 (FIGS. 35 and 40) are preferably provided to allow connections through external wiring where required. For clarity of presentation, the details of the electrical connections both between rail 338 and connectors 342 and between rail 340 and connectors 344, as well as to multiconnector sockets 346, have been omitted from the Figures.

It is a particular feature of a preferred embodiment of modules 314 that connectors 342 and 344 allow adaptable electrical grouping of connected modules. By subdividing the power supply of a large area ozone generator into multiple small areas, it is possible to employ a number of low-current high-voltage transformers, thereby avoiding both the safety hazards and legal restrictions associated with high-current high-voltage systems. When, on the other hand, a high-current supply is available, the same modules can readily be rearranged to provide common parallel connection of all of the modules. An example of one suitable arrangement of connectors 342, 344 and their use will now be described with reference to FIGS. 40–42.

In this example, it should be noted that the complementary interlocking forms of sides 322 and 324 are made identical such that, if one module 314 is rotated 180° about a line parallel to sides 322 and 324 (referred to below as "flipped"), the flipped side 322 will interlock with side 322 of an un-flipped module 314. Similarly, the forms of ends 326 and 328 are made identical such that, if one module 314 is rotated 180° about a line parallel to ends 326 and 328 (referred to below as "inverted"), the inverted end 326 will interlock with end 326 of an un-inverted module 314.

Figure 40:
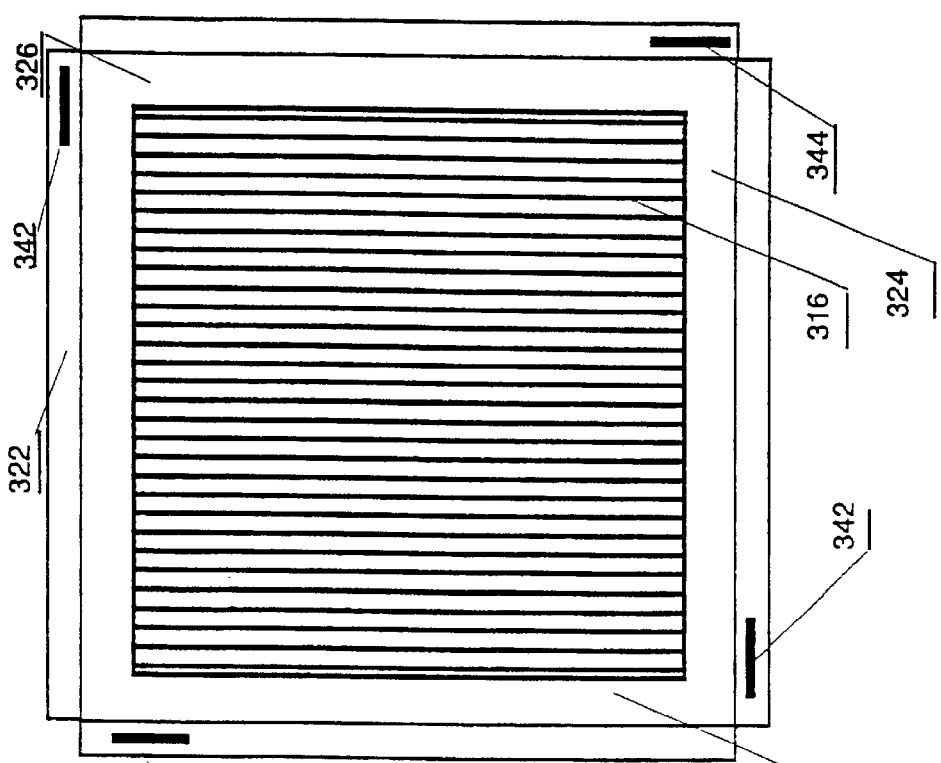
FIG. 40 is a schematic front view of a module from FIG. 34 showing a possible configuration of electrical connections.

FIG. 40 shows module 314 with asymmetrically located connectors 342 at the upper end of side 322 and the lower end of side 324. Similarly, connectors 344 are asymmetrically located at the right side of end 326 and the left side of end 328.

It will readily be understood that if two modules of this design are assembled side-by-side, no contact will be made between connectors 342 of the attached sides. If, on the other hand, one of the modules is flipped, connectors 342 are brought into overlapping positions so that they make electrical contact when assembled.

Similarly, if two modules of this design are assembled one-above-the-other, no contact will be made between connectors 344 of the attached ends. If one of the modules is inverted, connectors 344 are brought into overlapping positions so that they make electrical contact when assembled.

Figure 41:
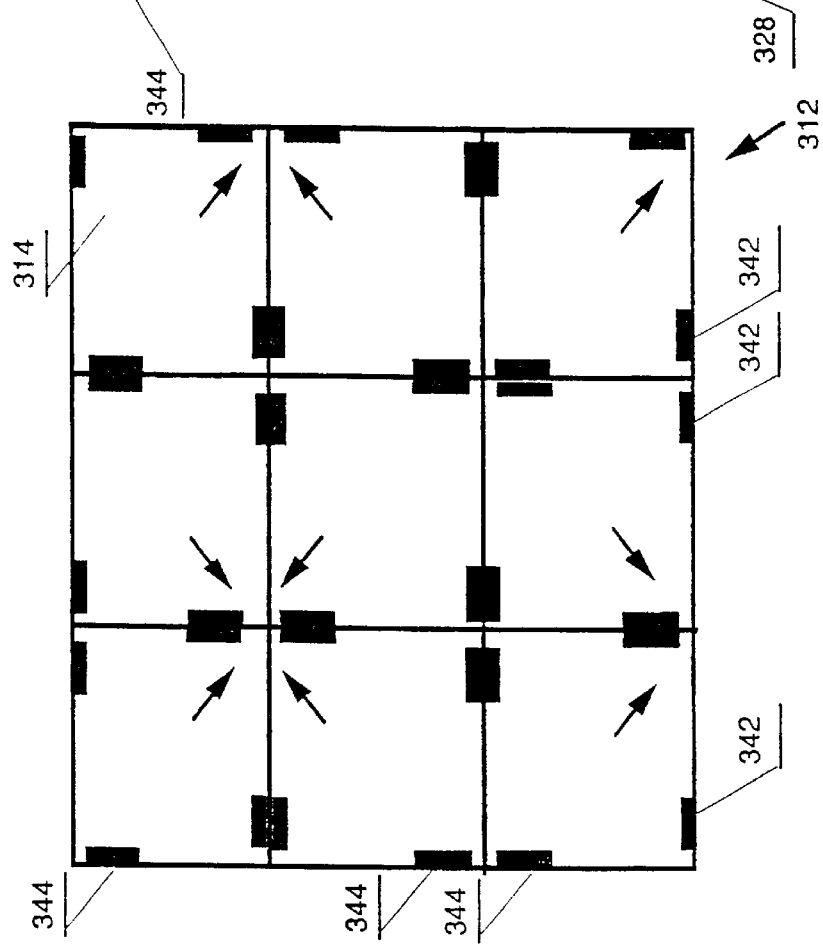
FIGS. 41 and 42 are schematic representations of two possible ways of assembling a number of modules as in FIG. 40.

FIG. 41 shows an assembly 312 made up of a 3×3 array of modules 314. For ease of reference, the relative orientation of each module is represented by the direction of an arrow. Each module is flipped relative to its horizontal neighbors and inverted relative to its vertical neighbors. As a result, continuous connections are formed between connectors 342 horizontally across the entire assembly, and between connectors 344 vertically across the entire assembly. The assembly can therefore be activated simply by connecting three exposed connectors 342 to one pole of the supply and three exposed connectors 344 to the other pole of the supply.

Figure 42:
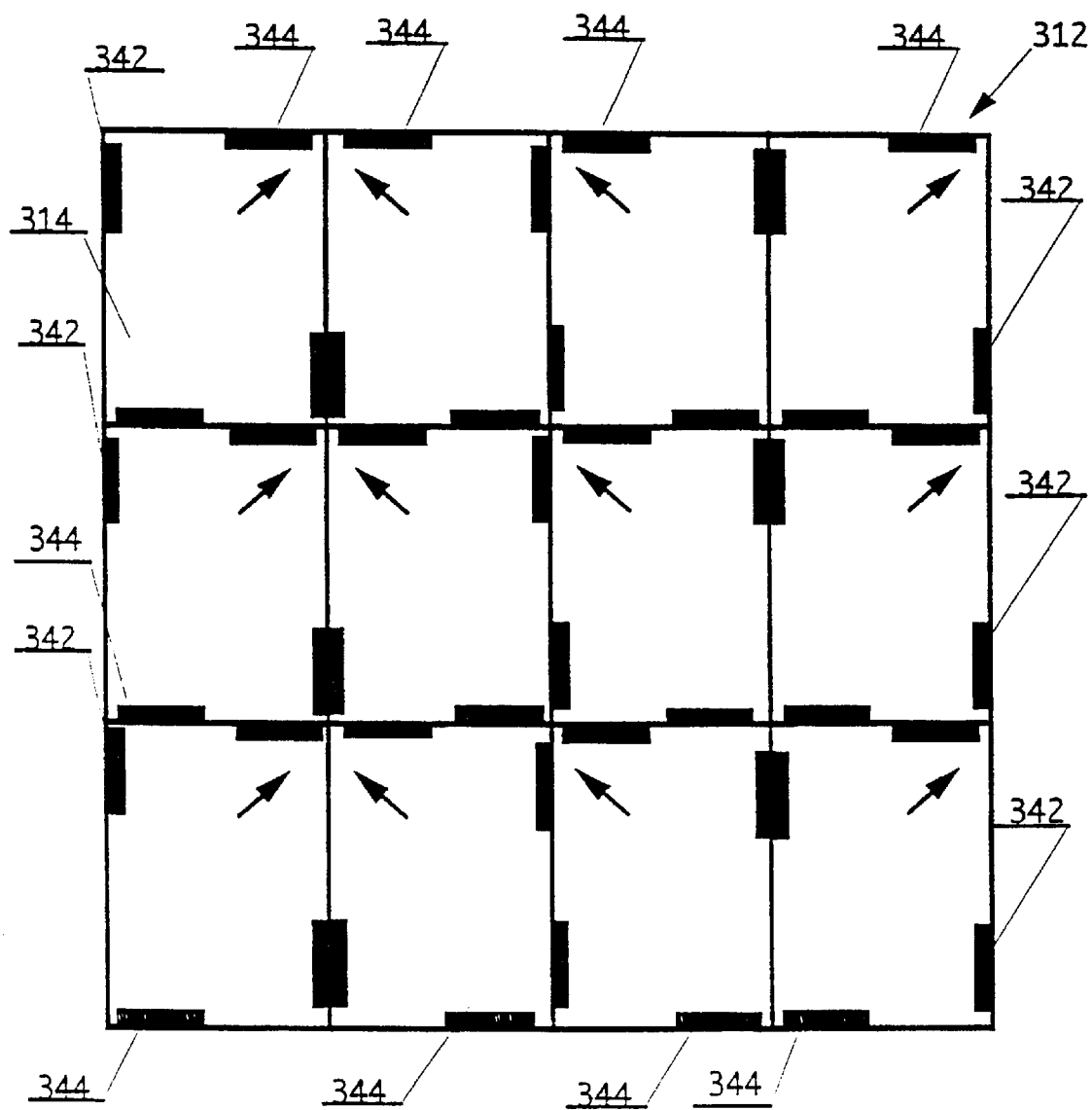

FIG. 42 shows an alternative assembly, this time a 3×4 array, of modules 314. In this case, no inversion of modules 314 has been employed. As a result, no vertical connections are formed. Similarly, flipping has been performed selectively to form connections of pairs of modules 314. As a result, assembly 312 is electrically subdivided into small sub-units of pairs of modules 314, each of which has all the advantages of low current requirements mentioned above. Parenthetically, it should be noted that external wiring is required in this case to connect to rail 340 of the middle row of modules by attachment to multiconnectors 346.

It should be noted that the entire structure of modules 314 is preferably integrally formed from molded polyvinyldifluoride with appropriately positioned electrically conductive implants. The choice of conductive material is not critical, but may typically be aluminum.

It will be understood that assembly 312 operates in conjunction with some type of flow generator (not shown) for generating a flow of oxygen containing gas through the assembly in a direction substantially perpendicular to the plane of the electrode arrays. Any type of flow generator, either dedicated to the ozone generator or non-dedicated, may be used.

It should be appreciated that the deployment of the electrodes in a plane perpendicular to the direction of gas flow results in homogeneous cooling of the electrodes along their entire length during operation of the ozone generator. This phenomenon markedly reduces thermo-dissociation of the ozone.

Figure 43:
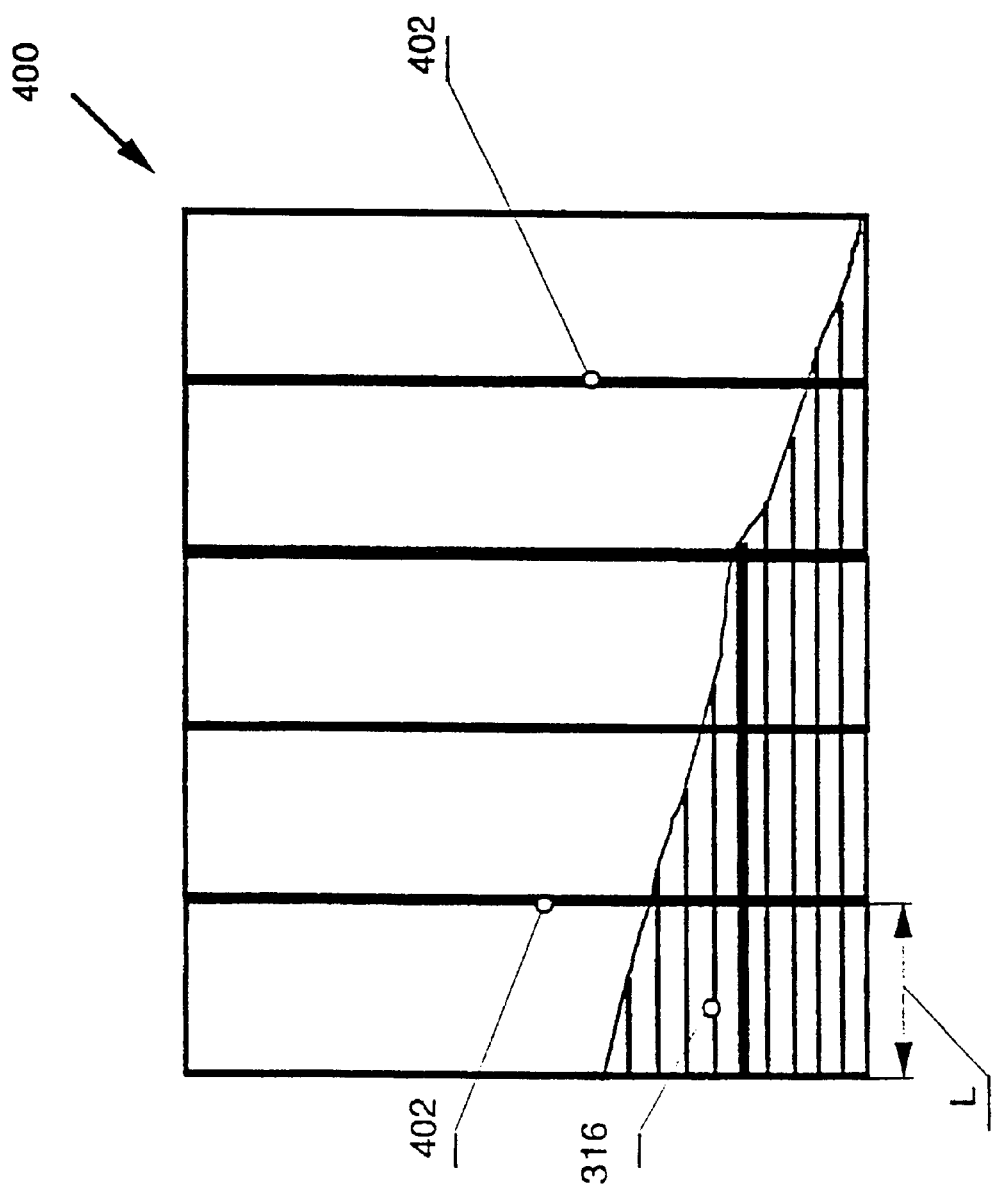
FIG. 43 is a schematic front view of an alternative modular ozone generator assembly, constructed and operative according to the teachings of the present invention.

Turning now to FIG. 43, this illustrates a variant 400 of modular frame-ozonator assembly 312. Assembly 400 is generally similar to assembly 312, differing primarily in that the modules 402 are formed as strips elongated in a direction perpendicular to the electrodes. In all other respects, features of assembly 400 may be readily understood by analogy to assembly 312 described above.

Finally, turning to FIGS. 44 and 45, a high concentration frame-type ozone generator, generally designated 500, constructed and operative according to the teachings of the present invention, will now be described.

Ozone generator 500 has a number of frames 502 each made up of an array of elongated electrodes deployed in substantially parallel, spaced relation to each other similar to those described above. Frames 502 are deployed, spaced apart along a flue 504 of square section so that they cover the entire cross-sectional area of the flue. Flue 504 is mounted within a substantially closed cylindrical casing 506 so as to define peripheral gas flow ducts 508.

Casing 506 is features an inlet 510 and an outlet 512. Near inlet 510, a power supply 514 supplies a motor 516 which drives a fan 518 via a drive shaft 520. A partition 522 defines a small aperture 524 around drive shaft 520 and serves to separate the inlet region containing power supply 514 and motor 516 from the operating volume of ozone generator 500.

In operation, fan 518 generates a dual flow pattern: Firstly, it drives gas within the operating volume in a circulating flow along flue 504 and back along peripheral ducts 508 so that the gas recirculates through frames 502. Additionally, the suction effect at the rear of fan 518 draws in gas from inlet 510 via aperture 524, producing a corresponding through-flow of gas out through outlet 512. By correctly configuring ozone generator 500, and more specifically, by adjusting the size of aperture 524, the volumetric flow rate $V_0$ of the through-flow is set to be significantly less than the volumetric flow rate $V_1$ of the recirculation flow. Preferably, $V_1$ is at least ten times greater than $V_0$ so as to generate homogeneous mixtures with a relatively high concentration of ozone in a carrier gas.

Considerable heat is generated during operation of the ozone generator. In some cases, unassisted air cooling of the gas within ducts 508 through the walls of casing 506 may be sufficient. Alternatively, an active cooling system is provided for cooling the walls of casing 506. One example of such a system is a water circulation cooling system represented by cooling pipes 526.

The positioning of fan 518 relative to aperture 524 helps to ensure that no possibly damaging ozone flows back into the region containing the power supply and motor.

Preferably, inlet 510 is provided with a filter and/or an electrostatic precipitator for removing dust and other small particles from the incoming air, thereby safeguarding the performance of ozone generator 500.

It will be appreciated that the above descriptions are intended only to serve as examples, and that many other embodiments are possible within the spirit and the scope of the present invention.

What is claimed is:

1. An apparatus for treating a product with ozone-containing gas, the apparatus comprising:
   (a) a container having an inner volume for containing the product;
   (b) an ozone generator for supplying ozone-containing gas to said volume; and
   (c) a flow generating system configured so as to generate a flow of the ozone-containing gas which alternates between a first direction and a second direction opposite to said first direction.

2. The apparatus of claim 1, further comprising a cooling system for cooling at least a surface layer of the product prior to treatment sufficiently to cause condensation of ozone-containing water vapor on said surface layer.

3. The apparatus of claim 1, further comprising a cooling system for cooling at least a surface layer of the product prior to treatment sufficiently to cause freezing of ozone-containing water vapor on said surface layer.

4. The apparatus of claim 1 wherein the product is water, the apparatus further comprising a water management system for generating a moving film of water within the container.

5. The apparatus of claim 1 wherein the product is water, the apparatus further comprising:
   (a) a spray generator for producing a spray of water moving in a first direction within said container; and
   (b) a flow generating system for generating a flow of the ozone-containing gas in a direction substantially opposite to said first direction.

6. The apparatus of claim 1, further comprising a catalytic filter associated with said container for removing ozone from the ozone-containing gas prior to opening of said container.

7. The apparatus of claim 1, further comprising a pressure-wave generator for generating pressure waves within said volume so as to enhance effectiveness of the ozone treatment.

8. A method for batch treatment of a product with a potentially harmful gas, the method comprising:
   (a) providing first and second treatment chambers;
   (b) treating a first batch of the product with a quantity of the gas within said first treatment chamber;
   (c) positioning a second batch of the product within said second treatment chamber; and
   (d) transferring from said first treatment chamber to said second treatment chamber at least part of said quantity of the gas.

9. The method of claim 8, wherein the potentially harmful gas is an ozone-containing gas.

10. The method of claim 9, wherein said transferring is performed through an ozone generator so as to further increase a proportion of ozone in the ozone-containing gas.

11. The method of claim 9, further comprising transferring gas from said second treatment chamber to said first treatment chamber through a catalytic filter.

12. The method of claim 9, further comprising generating pressure-waves within said first treatment chamber so as to enhance effectiveness of the ozone treatment.

13. The method of claim 9, further comprising, prior to said treatment, cooling at least a surface layer of the product sufficiently to cause condensation of ozone-containing water vapor on said surface layer.

14. The method of 9, further comprising, prior to said treatment, cooling at least a surface layer of the product sufficiently to cause freezing of ozone-containing water vapor on said surface layer.

15. The method of claim 9, wherein said first and second treatment chambers share a common dividing wall which features at least one ozone generator and at least one catalytic filter.

16. The method of claim 15, wherein said at least one ozone generator has an inlet switchably communicating with either said first or said second treatment chamber and an outlet switchably communicating with either said first or said second treatment chamber.

17. The method of claim 16, wherein said at least one catalytic filter has an inlet switchably communicating with either said first or said second treatment chamber and an outlet switchably communicating with either said first or said second treatment chamber.

18. A high concentration frame-type ozone generator comprising:
   (a) a plurality of elongated electrodes deployed in substantially parallel, spaced relation to each other so as to form a substantially flat electrode array;
   (b) a casing substantially enclosing said electrode array, said casing having an inlet and an outlet; and
   (c) a flow system associated with said casing configured to generate:
      (i) a recirculating flow of gas within said casing recirculating through said electrode array, and
      (ii) a through-flow of gas in through said inlet and out through said outlet, said through-flow having a volumetric flow rate significantly less than a volumetric flow rate of said recirculation flow.

19. The ozone generator of claim 18, wherein said volumetric flow rate of said recirculation flow is at least ten times greater than said volumetric flow rate of said through-flow.

20. The ozone generator of claim 18, further comprising a cooling system associated with said casing for cooling said casing.

21. The ozone generator of claim 18, further comprising at least one additional electrode array similar to, and deployed parallel to, said electrode array such that said recirculation flow passes sequentially through said electrode array and said additional electrode array.

22. An apparatus for treating a product with ozone-containing gas, the apparatus comprising:
   (a) a container having an inner volume for containing the product;
   (b) an ozone generator for supplying ozone-containing gas to said volume; and
   (c) a cooling system for cooling at least a surface layer of the product prior to treatment sufficiently to cause condensation of ozone-containing water vapor on said surface layer.

23. The apparatus of claim 22, wherein said cooling system is configured to cool said surface layer of the product sufficiently to cause freezing of ozone-containing water vapor on said surface layer.

24. The apparatus of claim 22, further comprising a pressure-wave generator for generating pressure waves within said volume so as to enhance effectiveness of the ozone treatment.

25. An apparatus for treating water with ozone-containing gas, the apparatus comprising:
  (a) a container having an inner volume;
  (b) an ozone generator for supplying ozone-containing gas to said volume;
  (c) a spray generator for producing a spray of water moving in a first direction within said container; and
  (iv) a flow generating system for generating a flow of the ozone-containing gas in a direction substantially opposite to said first direction.

26. The apparatus of claim 25, further comprising a pressure-wave generator for generating pressure waves within said volume so as to enhance effectiveness of the ozone treatment.

* * * * *